(12) United States Patent
Hurt et al.

(10) Patent No.: US 8,809,317 B2
(45) Date of Patent: *Aug. 19, 2014

(54) ANTIVIRAL COMPOUNDS

(75) Inventors: Clarence R. Hurt, Los Altos, CA (US); Vishwanath Lingappa, San Francisco, CA (US); Beverly Freeman, Albany, CA (US); Andy Atuegbu, Dublin, CA (US); Anatoliy Kitaygorodskyy, San Francisco, CA (US)

(73) Assignee: Prosetta Antiviral Inc., San Francisco, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/433,378

(22) Filed: Mar. 29, 2012

(65) Prior Publication Data

US 2012/0302556 A1    Nov. 29, 2012

Related U.S. Application Data

(63) Continuation-in-part of application No. 13/099,006, filed on May 2, 2011, and a continuation-in-part of application No. 13/316,423, filed on Dec. 9, 2011.

(60) Provisional application No. 61/468,614, filed on Mar. 29, 2011, provisional application No. 61/477,203, filed on Apr. 20, 2011, provisional application No. 61/479,351, filed on Apr. 26, 2011, provisional application No. 61/514,825, filed on Aug. 3, 2011.

(51) Int. Cl.
*C07D 417/10* (2006.01)
*C07D 279/20* (2006.01)
*A61K 31/5415* (2006.01)

(52) U.S. Cl.
USPC .................. 514/210.2; 514/225.2; 514/224.8; 544/35; 544/37; 544/38

(58) Field of Classification Search
USPC ........ 544/35, 37, 38; 514/210.2, 225.2, 224.8
See application file for complete search history.

(56) References Cited

FOREIGN PATENT DOCUMENTS

GB        2083488 A  *  3/1982

* cited by examiner

*Primary Examiner* — Kahsay Habte
(74) *Attorney, Agent, or Firm* — Morgan, Lewis & Bockius LLP

(57) ABSTRACT

Compounds and methods for preventing and treating viral infections are provided. In some embodiments, novel compounds broad-spectrum antiviral activity are provided. In more specific embodiments, the compounds and methods are effective against viruses such as Venezuelan Equine Encephalitis, West Nile Virus, and Hepatitis C.

24 Claims, No Drawings

ANTIVIRAL COMPOUNDS

1 CROSS REFERENCE TO RELATED APPLICATIONS

This application is a continuation-in-part of U.S. Pat. application Ser. No. 13/099,006 filed 2 May 2011 and is a continuation-in-part of Ser. No. 13/316,423 filed 9 Dec. 2011, and claims priority to provisional U.S. Patent Application Ser. No. 61/468,614 filed 29 Mar. 2011, 61/477,203 filed 20 Apr. 2011, 61/479,351 filed 26 Apr. 2011, and 61/514,825 filed 3 Aug. 2011, the entire disclosure of U.S. Patent Application Ser. No. 61/468,614 filed 29 Mar. 2011 is incorporated herein by reference in its entirety and for all purposes.

2 BACKGROUND OF THE INVENTION 2.1. Field of the Invention

The present invention provides compositions and methods for preventing and treating viral infections. The present invention thus has applications in the areas of medicine, pharmacology, virology, and medicinal chemistry.

2.2. The Related Art

Few good options are available for preventing or treating viral infections. The vast majority of antiviral drugs interfere with viral replication through the inhibition of transcription of the viral genome. Commonly these drugs inhibit a specific protein involved in viral genomic transcription, such as a polymerase or transcriptase; which often produces unwanted toxicity, since viruses depend largely on host factors for viral genomic replication. Moreover, given the highly specific nature of the target, small mutations in the viral genome are often sufficient to create viral strains that are resistant to chemotherapeutics. In addition, since the drugs inhibit active viral replication, they cannot eliminate virus that is latent or sequestered in the host; thus, patients are forced to take antivirals and endure their toxic effects for long periods if not indefinitely. Not surprisingly, patients on such regimens cannot continue treatment, and remain infected as well as providing a potentially continuing source of additional infections.

Thus there is a need for better antiviral chemotherapeutics and more effective strategies for identifying such chemotherapeutics. The need is especially urgent for those suffering from chronic and debilitating viral infections, such as human immunodeficiency virus (HIV) and hepatitis C (HCV), for which no good treatment exists for the reasons noted above.

But new viral threats are also on the horizon. The steady encroachment of civilization into the most remote regions of the globe has introduced the risk of exotic viral infections to the population at large. Each passing year brings an increasing number of reports of infections by hemorragic fevers, such as Ebola virus (EBOV), Marburg virus (Marburg), and Rift Valley Fever virus (RVFV). Still other viral infections can cause potentially debilitating effects, such as recurrent fevers, joint pain, and fatigue; these include: Punta Toro Virus (PTV), West Nile virus (WNV), chikungunya virus (CHK), Easter Equine Encephalitis virus (EEEV), Western Equine Encephalitis virus (WEEV), Lhasa virus (LASV), and Dengue virus (DENV).

By way of example, one of the additional "new" viruses (that is, new with respect to the industrialized world) is Venezuelan Equine Encephalitis virus (also called Venezuelan equine encephalomyelitis, VEEV). VEEV is a mosquito-borne viral disease of all equine species, including horses, asses (wild and domestic), and zebras. Equines infected with VEEV may show one or more of the following signs: fever, depression, loss of appetite weakness, and central nervous system disorders (lack of coordination, chewing movements, head pressing, "sawhorse" stance, circling, paddling motion of the limbs, and convulsions). In some cases, horses infected with VEEV may show no clinical signs before dying. The clinical signs of VEEV can be confused with those of other diseases that affect the central nervous system. These include eastern equine encephalitis, western equine encephalitis, African horse sickness, rabies, tetanus, and bacterial meningitis. VEE might also be mistaken for toxic poisoning. Definitive diagnosis can be made by isolating the virus in a laboratory or by testing blood for the presence of antibodies to the virus.

Humans also can contract this disease. Healthy adults who become infected by the virus may experience flu-like symptoms, such as high fevers and aches; and those having weakened immune systems, as well as the young and elderly, can become more severely ill or even die.

The virus that causes VEEV is transmitted primarily by mosquitoes that bite an infected animal and then bite and feed on another animal or human. The speed with which the disease spreads depends on the subtype of the VEEV virus and the density of mosquito populations. Enzootic subtypes of VEEV are diseases endemic to certain areas. Generally these serotypes do not spread to other localities. Enzootic subtypes are associated with the rodent-mosquito transmission cycle. These forms of the virus can cause human illness but generally do not affect equine health. Epizootic subtypes, on the other hand, can spread rapidly through large populations. These forms of the virus are highly pathogenic to equines and can also affect human health. Equines, rather than rodents, are the primary animal species that carry and spread the disease. Infected equines develop an enormous quantity of virus in their circulatory system. When a blood-feeding insect feeds on such animals, it picks up this virus and transmits it to other animals or humans. Although other animals, such as cattle, swine, and dogs, can become infected, they generally do not show signs of the disease or contribute to its spread.

Naturally occurring outbreaks of VEEV are rare. In 1936, VEEV was first recognized as a disease of concern in Venezuela following a major outbreak of equine encephalomyelitis. From 1936 to 1968, equines in several South American countries suffered devastating outbreaks. In 1969, the disease moved north throughout Central America, finally reaching Mexico and Texas in 1971. The highly pathogenic form of VEEV has not occurred in the United States since 1971. However, in 1993 an outbreak of VEEV in the State of Chiapas, Mexico, prompted the U.S. Department of Agriculture to temporarily increase its surveillance activities and tighten its quarantine requirements for equine species entering the United States from Mexico. During outbreaks, the most effective way to prevent further spread of disease is to quarantine infected equines. Controlling mosquito populations through pesticide treatments and eliminating insect-breeding sites will also enhance disease control. These measures should be accompanied by a large-scale equine immunization program. Equines in the United States should be vaccinated for VEE only when there is a serious threat that the disease could spread to this country.

Similar to VEE is West Nile virus (WNV), which was mentioned above. West Nile virus is named for a district in Uganda where the virus was first identified in humans in 1937. Outbreaks of the virus have occurred in a number of countries throughout Europe, the Middle East, Africa, Central Asia, and Australia, since that time. WNV was first detected in the Western Hemisphere in 1999, and since then the disease has spread across North America, Mexico, Puerto Rico, the Dominican Republic, Jamaica, Guadeloupe, and El Salvador. Symptoms range from a mild, flu-like illness (fever, headache, muscle and joint pain) and a red, bumpy rash, to meningitis. In rare cases those infected will develop encephalitis, which can include high fever, a stiff neck, disorientation, paralysis, convulsions, coma, and death in about ten percent of cases.

No cure or treatment is available for either VEEV or WNV, or the other viruses listed above; so public health experts emphasize prevention by avoiding areas where the disease has been detected or where disease vectors (usually mosquitoes) have been identified. However, that approach is becoming less reasonable as the world population grows. Moreover, some officials fear that one or both of these diseases, or other similar viruses in the toga- and flaviviridae, could be "weaponized" by a hostile government or terrorist organization to immobilize military personnel or important segments of the population in an attack.

To make matters still more complicated, the above-mentioned viral threats span almost all of the recognized viral families, including the bunyaviruses, flaviviruses, filoviruses, arenaviruses, and togaviruses. Since viral families are defined in significant part by their differences in mechanism for genomic replication, therapeutic strategies that are focused on inhibiting genomic replication will be inadequate for large outbreaks of new, and especially weaponized, viruses.

PCT Publication WO 2008/124550 discloses small molecule therapeutics having "broad spectrum" antiviral properties. Nevertheless, there remains an acute need to provide medicinal treatments for viral diseases. The present invention meets these and other needs.

3 SUMMARY OF EMBODIMENTS OF THE INVENTION

In one embodiment, the present invention provides compounds, compositions, and methods for treating various viruses. In a first aspect, the present invention provides compounds having the structure:

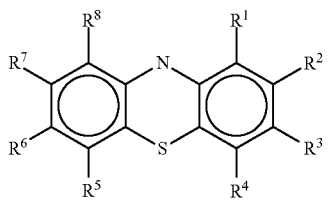

and their pharmaceutically acceptable salts, hydrates, and coordination compounds. $R^1$, $R^2$, $R^4$, $R^5$, $R^7$, and $R^8$ are selected independently from the group consisting of: hydrogen, halo, cyano, nitro, thio, amino, carboxyl, formyl, and optionally substituted alkyl, alkylcarbonyloxy, arylcarbonyloxy, heteroarylcarbonyloxy, cycloalkylcarbonyloxy, cycloheteroalkylcarbonyloxy, aralkycarbonyloxy, heteroaralkylcarbonyloxy, (cycloalkyl)alkylcarbonyloxy, (cycloheteroalkyl)alkylcarbonyloxy, alkylcarbonyl, arylcarbonyl, heteroarylcarbonyl, cycloalkycarbonyl, cycloheteroalkycarbonyl, aralkylcarbonyl, heteroaralkylcarbonyl, (cycloalkyl)alkylcarbonyl, (cycloheteroalkyl)alkylcarbonyl, alkylaminocarbonyl, arylaminocarbonyl, aralkylaminocarbonyl, heteroarylaminocarbonyl, heteroaralkylaminocarbonyl, alkylcarbonylamino, arylcarbonylamino, heteroarylcarbonylamino, cycloalkylcarbonylamino, cycloheteroalkylcarbonylamino, aralkylcarbonylamino, heteroar alkylcarbonylamino, (cycloalkyl)alkylcarbonylamino, (cycloheteroalkyl)alkylcarbonylamino, dialkylamino, arylamino, diarylamino, aralkylamino, diaralkylamino, heteroarylamino, diheteroarylamino, heteroaralkylamino, diheteroaralkylamino, alkylsulfonyl, arylsulonyl, heteroarylsuony, cycloalkylsulfonyl, aralkycarbonylthioooxy, carbonylthio, heteroaralkylcarbonylthio, (cycloalkyloxy)carbonylthio, (cycloheteroalkyl)alkylcarbonylthio, alkyloxycarbonyl, aryloxycarbonyl, heteroaryloxycarbonyl, cycloalkyloxycarbonyl, cycloheteroalkyloxycarbonyl, aralyoxycarbonyloxloxycarbonyl, heteroaralkyloxycarbony, (cycloalkyl) alkyloxycarbonyl, (cycloheteroalkyl)alkyloxycarbony, iminoalkyl, iminocycloalky, iminocycloheteroalkyl, iminoaralkyl, iminoheteroaralkyl, (cycloalkyl)iminoalkyl, and (cycloheteroalkyl)iminoalkyl. $R^3$ and $R^6$ are selected independently from the group consisting of: oxo, thiocarbonyl, imino, optionally substituted dialkylimino, diarylimino, di-heteroarylimino, alkylarylimino, alkylheteroarylimino, arylheteroarylimino, alkyloxyalkylamino, di-(alkyloxyalkyl)amino, alkylthioalkylamino, di-(alkylthioalkyl)amino, alkylaminoalkylamino, di-(alkylaminoalkyl)amino, aryloxyalkylamino, di-(aryloxyalkyl)amino, arylthioalkylamino, di-(arylthioalkyl)amino, arylaminoalkylamino, di-(arylaminoalkyl)amino, heteroaryloxyalkylamino, di-(heteroaryloxyalkyl)amino, heteroarylthioalkylamino, di-(heteroarylthioalkyl)amino, heteroarylaminoalkylamino, di-(heteroarylaminoalkyl)amino, and cycloalkylamino. At least one of $R^3$ and $R^6$ is selected from the group consisting of: alkyloxyalkylamino, di-(alkyloxyalkyl)amino, alkylthioalkylamino, di-(alkylthioalkyl)amino, alkylaminoalkylamino, di-(alkylaminoalkyl)amino, aryloxyalkylamino, di-(aryloxyalkyl)amino, arylthioalkylamino, di-(arylthioalkyl)amino, arylaminoalkylamino, di-(arylaminoalkyl)amino, heteroaryloxyalkylamino, di-(heteroaryloxyalkyl)amino, heteroarylthioalkylamino, di-(heteroarylthioalkyl)amino, heteroarylaminoalkylamino, and di-(heteroarylaminoalkylene) amino.

In a more specific embodiment, $R^3$ is selected from the group consisting of: alkyloxyalkylamino, di-(alkyloxyalkyl) amino, alkylthioalkylamino, di-(alkylthioalkyl)amino, alkylaminoalkylamino, di-(alkylaminoalkyl)amino, aryloxyalkylamino, di-(aryloxyalkyl)amino, arylthioalkylamino, di-(arylthioalkyl)amino, arylaminoalkylamino, di-(arylaminoalkylene)amino, heteroaryloxyalkylamino, di-(heteroaryloxyalkylene)amino, heteroarylthioalkylamino, di-(heteroarylthioalkyl)amino, erHetoarylaminoalkylamino, and di-(heteroarylaminoalkyl)amino.

In still more specific embodiments from those just described, at least one of $R^1$ and $R^8$ is selected from the group consisting of: halo, nitro, cyano, carboxyl, formyl, and optionally substituted alkyl; more specifically at least one of $R^1$ and $R^8$ is selected from the group consisting of: halo, carboxyl, and optionally substituted alkyl; and still more specifically, at least one of $R^1$ and $R^8$ is selected from the group consisting of: halo, carboxyl, and optionally substituted alkyl.

Yet more specific embodiments are those in which at least one of $R^1$ and $R^8$ is halo; still more specifically least one of $R^1$ and $R^8$ is fluoro or least one of $R^1$ and $R^8$ is chloro.

In other more specific embodiments, $R^1$ and $R^8$ are both halo; more specifically $R^1$ and $R^8$ are both fluoro or $R^1$ and $R^8$ are both chloro.

In still other embodiments, at least one of $R^1$ and $R^8$ is selected from the group consisting of: halo, carboxyl, and optionally substituted alkyl. Among these compounds, more specific embodiments include those wherein at least one of $R^1$ and $R^8$ is selected from the group consisting of: halo, carboxyl, and optionally substituted alkyl.

Yet more specific embodiments are those in which at least one of $R^1$ and $R^8$ is halo; still more specifically least one of $R^1$ and $R^8$ is fluoro or least one of $R^1$ and $R^8$ is chloro.

In other more specific embodiments, $R^1$ and $R^8$ are both halo; more specifically $R^1$ and $R^8$ are both fluoro or $R^1$ and $R^8$ are both chloro.

In another aspect, the invention provides a method for treating a viral disease in a mammal afflicted with such disease, comprising administering to such mammal a therapeutically effective amount of a compound of described herein.

4 DETAILED DESCRIPTION OF SOME EMBODIMENTS OF THE INVENTION

4.1 Definitions

The following terms are used herein as defined below unless specifically stated otherwise:

Optionally substituted refers to the replacement of hydrogen with a univalent or divalent radical. Suitable substitution groups include, for example, hydrooxyl, nitro, amino, imino, cyano, halo, thio, thioamido, amidino, oxo, oxamidino, methoxamidino, imidino, guanidino, sulfonamido, carboxyl, formyl, loweralkyl, haloloweralkyl, loweralkoxy, haloloweralkoxy, loweralkoxyalkyl, alkylcarbonyl, arylcarbonyl, aralkylcarbonyl, heteroarylcarbonyl, heteroaralkylcarbonyl, alkylthio, aminoalkyl, cyanoalkyl, and the like as defined herein. The substitution group can itself be substituted. The group substituted onto the substitution group can be, for example, carboxyl, halo; nitro, amino, cyano, hydroxyl, loweralkyl, loweralkoxy, aminocarbonyl, —SR, thioamido, —SO$_3$H, —SO$_2$R or cycloalkyl, where R is typically hydrogen, hydroxyl or loweralkyl. When the substituted substituent includes a straight chain group, the substitution can occur either within the chain (e.g., 2-hydroxypropyl, 2-aminobutyl, and the like) or at the chain terminus (e.g., 2-hydroxyethyl, 3-cyanopropyl, and the like). Substituted substitutents can be straight chain, branched or cyclic arrangements of covalently bonded carbon or heteroatoms.

Loweralkyl as used herein refers to branched or straight chain alkyl groups comprising one to ten carbon atoms that independently are unsubstituted or substituted, e.g., with one or more halogen, hydroxyl or other groups. Examples of loweralkyl groups include, but are not limited to, methyl, ethyl, propyl, isopropyl, n-butyl, t-butyl, n-hexyl, neopentyl, trifluoromethyl, pentafluoroethyl, and the like.

Alkylenyl refers to a divalent straight chain or branched chain saturated aliphatic radical having from 1- to 20 carbon atoms. Typical alkylenyl groups employed in compounds of the present invention are loweralkylenyl groups that have from 1 to about 6 carbon atoms in their backbone.

Alkenyl refers herein to straight chain, branched, or cyclic radicals having one or more double bonds and from 2 to 20 carbon atoms.

Alkynyl refers herein to straight chain, branched, or cyclic radicals having one or more triple bonds and from 2 to 20 carbon atoms.

Haloloweralkyl refers to a loweralkyl radical substituted with one or more halogen atoms.

Loweralkoxy as used herein refers to RO— wherein R is loweralkyl. Representative examples of loweralkoxy groups include methoxy, ethoxy, t-butoxy, trifluoromethoxy and the like.

Loweralkylhio as used herein refers to RS— wherein R is loweralkyl.

Alkoxyalkyl refers to the group -alk$_1$-O-alk$_2$, where alk$_1$ is alkylenyl or alkenyl, and alk$_2$ is alkyl or alkenyl.

Loweralkoxyalkyl refers to an alkoxyalkyl as defined above, where alk$_1$ is loweralkylenyl or loweralkenyl, and alk$_2$ is loweralkyl or loweralkenyl.

Aryloxyalkyl refers to the group alkylenyl-O-aryl. The term Aralkoxyalkyl refers to the group alkylenyl-O-aralkyl, where aralkyl is a loweraralkyl.

Cycloalkyl refers to a mono- or polycyclic, loweralkyl substituent. Typical cycloalkyl substituents have from 3 to 8 backbone (i.e., ring) atoms in which each backbone atom is optionally substituted carbon. When used in context with cycloalkyl substituents, the term polycyclic refers herein to fused, non-fused cyclic carbon structures and spirocycles. Examples of cycloalkyl groups include, but are not limited to, cyclopropyl, cyclobutyl, cyclopentyl, cyclohexyl, adamantyl, bornyl, norbornyl, and the like.

Cycloheteroalkyl refers herein to cyclic substituents that have from 1 to 5, and more typically from 1 to 4 heteroatoms (i.e., non-carbon atoms such as nitrogen, sulfur, and oxygen) in the ring structure, with the balance of atoms in the ring being optionally substituted carbon. Representative heterocycloalkyl moieties include, for example, cycloalkylamino substituents such as piperazinyl, piperidinyl, pyrrolidinyl, methylpryolidinyl, pyrrolidinone-yl, morpholino, and the like.

(Cycloalkyl)alkyl and (Cycloheteroalkyl)alkyl refer to alkyl chains substituted with cycloalkyl and cycloheteroalkyl groups respectively.

Haloalkoxy refers to an alkoxy radical substituted with one or more halogen atoms. The term haloloweralkoxy refers to a loweralkoxy radical substituted with one or more halogen atoms.

Halo refers herein to a halogen radical, such as fluorine, chlorine, bromine, or iodine.

Aryl refers to monocyclic and polycyclic aromatic groups, or fused ring systems having at least one aromatic ring, having from 3 to 14 backbone carbon atoms. Examples of aryl groups include without limitation phenyl, naphthyl, dihydronaphtyl, tetrahydronaphthyl, and the like.

Aralkyl refers to an alkyl group substituted with an aryl group. Typically, aralkyl groups employed in compounds of the present invention have from 1 to 6 carbon atoms incorporated within the alkyl portion of the aralkyl group. Suitable aralkyl groups employed in compounds of the present invention include, for example, benzyl, picolyl, and the like.

Heteroaryl refers herein to aryl groups having from one to four heteroatoms as ring atoms in an aromatic ring with the remainder of the ring atoms being aromatic or non-aromatic carbon atoms. When used in connection with aryl substituents, the term polycyclic refers herein to fused and non-fused cyclic structures in which at least one cyclic structure is aromatic, such as, for example, benzodioxozolo, naphthyl, and the like. Exemplary heteroaryl moieties employed as substituents in compounds of the present invention include pyridyl, pyrimidinyl, thiazolyl, indolyl, imidazolyl, oxadiazolyl, tetrazolyl, pyrazinyl, triazolyl, thiophenyl, furanyl, quinolinyl, purinyl, benzothiazolyl, benzopyridyl, and benzimidazolyl, and the like.

Amino refers herein to the group —NH$_2$. The term loweralkylamino refers herein to the group —NRR' where R and R' are each independently selected from hydrogen or loweralkyl. The term arylamino refers herein to the group —NRR' where R is aryl and R' is hydrogen, loweralkyl, aryl, or aralkyl. The term aralkylamino refers herein to the group —NRR' where R is aralkyl and R' is hydrogen, loweralkyl, aryl, or aralkyl. The terms heteroarylamino and heteroaralkylamino are defined by analogy to arylamino and aralkylamino.

Aminocarbonyl refers herein to the group —C(O)—NH$_2$. The terms loweralkylaminocarbonyl, arylaminocarbonyl, aralkylaminocarbonyl, heteroarylaminocarbonyl, and heteroaralkylaminocarbonyl refer to —C(O)NRR' where R and R' independently are hydrogen and optionally substituted loweralkyl, aryl, aralkyl, heteroaryl, and heteroaralkyl respectively by analogy to the corresponding terms above.

Thio refers to —SH. The terms loweralkylthio, arylthio, heteroarylthio, cycloalkylthio, cycloheteroalkylthio, aralkylthio, heteroaralkylthio, (cycloalkyl)alkylthio, and (cycloheteroalkyl)alkylthio refer to —SR, where R is optionally substituted loweralkyl, aryl, heteroaryl, cycloalkyl, cycloheteroalkyl, aralkyl, heteroaralkyl, (cycloalkyl)alkyl, and (cycloheteroalkyl)alkyl respectively.

Sulfonyl refers herein to the group —SO$_2$—. The terms loweralkylsulfonyl, arylsulfonyl, heteroarylsulfonyl, cycloalkylsulfonyl, cycloheteroalkylsulfonyl, aralkylsulfonyl, heteroaralkylsulfonyl, (cycloalkyl)alkylsulfonyl, and (cycloheteroalkyl)alkylsulfonyl refer to —SO$_2$R where R is optionally substituted loweralkyl, aryl, heteroaryl, cycloalkyl, cycloheteroalkyl, aralkyl, heteroaralkyl, (cycloalkyl)alkyl, and (cycloheteroalkyl)alkyl respectively.

Sulfinyl refers herein to the group —SO—. The terms loweralkylsulfinyl, arylsulfinyl, heteroarylsulfinyl, cycloalkylsulfinyl, cycloheteroalkylsulfinyl, aralkylsulfinyl, heteroaralkylsulfinyl, (cycloalkyl)alkylsulfinyl, and (cycloheteroalkyl)alkylsulfinyl refer to —SOR where R is optionally substituted loweralkyl, aryl, heteroaryl, cycloalkyl, cycloheteroalkyl, aralkyl, heteroaralkyl, (cycloalkyl)alkyl, and (cycloheteroalkyl)alkyl respectively.

Formyl refers to —C(O)H.

Carboxyl refers to —C(O)OH.

Carbonyl refers to the divalent group —C(O)—. The terms loweralkylcarbonyl, arylcarbonyl, heteroarylcarbonyl, cycloalkylcarbonyl, cycloheteroalkylcarbonyl, aralkycarbonyl, heteroaralkylcarbonyl, (cycloalkyl)alkylcarbonyl, and (cycloheteroalkyl)alkylcarbonyl refer to —C(O)R, where R is optionally substituted loweralkyl, aryl, heteroaryl, cycloalkyl, cycloheteroalkyl, aralkyl, heteroaralkyl, (cycloalkyl)alkyl, and (cycloheteroalkyl)alkyl respectively.

Thiocarbonyl refers to the group —C(S)—. The terms loweralkylthiocarbonyl, arylthiocarbonyl, heteroarylthiocarbonyl, cycloalkylthiocarbonyl, cycloheteroalkylthiocarbonyl, aralkylthiocarbonyloxlthiocarbonyl, heteroaralkylthiocarbonyl, (cycloalkyl)alkylthiocarbonyl, and (cycloheteroalkyl)alkylthiocarbonyl refer to —C(S)R, where R is optionally substituted loweralkyl, aryl, heteroaryl, cycloalkyl, cycloheteroalkyl, aralkyl, heteroaralkyl, (cycloalkyl)alkyl, and (cycloheteroalkyl)alkyl respectively.

Carbonyloxy refers generally to the group —C(O)—O—. The terms loweralkylcarbonyloxy, arylcarbonyloxy, heteroarylcarbonyloxy, cycloalkylcarbonyloxy, cycloheteroalkylcarbonyloxy, aralkylcarbonyloxy, heteroaralkylcarbonyloxy, (cycloalkyl)alkylcarbonyloxy, (cycloheteroalkyl)alkylcarbonyloxy refer to —C(O)OR, where R is optionally substituted loweralkyl, aryl, heteroaryl, cycloalkyl, cycloheteroalkyl, aralkyl, heteroaralkyl, (cycloalkyl)alkyl, and (cycloheteroalkyl)alkyl respectively.

Oxycarbonyl refers to the group —O—C(O)—. The terms loweralkyloxycarbonyl, aryloxycarbonyl, heteroaryloxycarbonyl, cycloalkyloxycarbonyl, cycloheteroalkyloxycarbonyl, aralkyloxy carbonyloxycarbonyl, heteroaralkyloxy carbonyl, (cycloalkyl)alkyloxycarbonyl, (cycloheteroalkyl)alkyloxycarbonyl refer to —O—C(O)R, where R is optionally substituted loweralkyl, aryl, heteroaryl, cycloalkyl, cycloheteroalkyl, aralkyl, heteroaralkyl, (cycloalkyl)alkyl, and (cycloheteroalkyl)alkyl respectively.

Carbonylamino refers to the group —NH—C(O)—. The terms loweralkylcarbonylamino, arylcarbonylamino, heteroarylcarbonylamino, cycloalkylcarbonylamino, cycloheteroalkylcarbonylamino, aralkylcarbonylamino, heteroaralkylcarbonylamino, (cycloalkyl)alkylcarbonylamino, and (cycloheteroalkyl)alkylcarbonylamino refer to —NH—C(O)R—, where R is optionally substituted loweralkyl, aryl, heteroaryl, cycloalkyl, cycloheteroalkyl, aralkyl, heteroaralkyl, (cycloalkyl)alkyl, or (cycloheteroalkyl)alkyl respectively. In addition, the present invention includes n-substituted carbonylamino (—NR'C(O)R), where R' is optionally substituted loweralkyl, aryl, heteroaryl, aralkyl, or heteroaralkyl and R retains the previous definition.

Carbonylthio refers to the group —C(O)—S—. The terms loweralkylcarbonylthio, arylcarbonylthio, heteroarylcarbonylthio, cycloalkylcarbonylthio, cycloheteroalkylcarbonylthio, aralkylcarbonylthio, heteroaralkylcarbonylthio, (cycloalkyl)alkylcarbonylthio, (cycloheteroalkyl)alkylcarbonylthio refer to —C(O)SR, where R is optionally substituted loweralkyl, aryl, heteroaryl, cycloalkyl, cycloheteroalkyl, aralkyl, heteroaralkyl, (cycloalkyl)alkyl, and (cycloheteroalkyl)alkyl respectively.

Guanidino or Guanidyl refers to moieties derived from guanidine, H$_2$N—C(=NH)—NH$_2$. Such moieties include those bonded at the nitrogen atom carrying the formal double bond (the 2-position of the guanidine, e.g., diaminomethyleneamino, ((H$_2$N)$_2$—C=NH—) and those bonded at either of the nitrogen atoms carrying a formal single bond (the 1- or 3-positions of the guanidine, e.g., H$_2$N—C(=NH)—NH—). The hydrogen atoms at either nitrogen can be replaced with a suitable substituent, such as loweralkyl, aryl, or loweraralkyl.

Amidino refers to the moieties R—C(=N)—NR'— (the radical being at the $N^1$ nitrogen) and R(NR')C=N— (the radical being at the $N^2$ nitrogen), where R and R' can be hydrogen, loweralkyl, aryl, or loweraralkyl.

Imino refers to the group —C(=NR)—, where R can be hydrogen or optionally substituted loweralkyl, aryl, heteroaryl, or heteroaralkyl respectively. The terms iminoloweralkyl, iminocycloalkyl, iminocycloheteroalkyl, iminoaralkyl, iminoheteroaralkyl, (cycloalkyl)iminoalkyl, (cycloiminoalkyl)alkyl, (cycloiminoheteroalkyl)alkyl, and (cycloheteroalkyl)iminoalkyl refer to optionally substituted loweralkyl, cycloalkyl, cycloheteroalkyl, aralkyl, heteroaralkyl, (cycloalkyl)alkyl, and (cycloheteroalkyl)alkyl groups that include an imino group, respectively.

Oximino refers to the group —C(=NOR)—, where R can be hydrogen (hydroximino) or optionally substituted loweralkyl, aryl, heteroaryl, or heteroaralkyl respectively. The terms oximinoloweralkyl, oximinocycloalkyl, oximinocycloheteroalkyl, oximinoaralkyl, oximinoheteroaralkyl, (cycloalkyl)oximinoalkyl, (cyclooximinoalkyl)alkyl, (cyclooximinoheteroalkyl)alkyl, and (cycloheteroalkyl)oximinoalkyl refer to optionally substituted loweralkyl, cycloalkyl, cycloheteroalkyl, aralkyl, heteroaralkyl, (cycloalkyl)alkyl, and (cycloheteroalkyl)alkyl groups that include an oximino group, respectively.

Methylene as used herein refers to an unsubstituted, mono-substituted, or disubstituted carbon atom having a formal sp³ hybridization (i.e., —CRR'—, where R and R' are hydrogen or independent substituents).

Methine as used herein refers to an unsubstituted or substituted carbon atom having a formal sp² hybridization (i.e., CR=or =CR—, where R is hydrogen or a substituent).

4.2 Compounds and Methods of the Invention

In a first aspect, the present invention provides novel compounds having the having the structure:

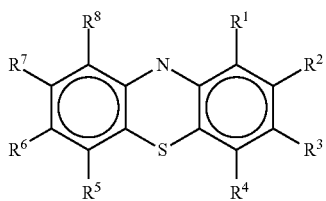

1 and their pharmaceutically acceptable salts, hydrates, and coordination compounds. The substituents $R^1$, $R^2$, $R^4$, $R^5$, $R^7$, and $R^8$ are selected independently from the group consisting of: hydrogen, halo, cyano, nitro, thio, amino, carboxyl, formyl, and optionally substituted alkyl, alkylcarbonyloxy, arylcarbonyloxy, heteroarylcarbonyloxy, cycloalkylcarbonyloxy, cycloheteroalkylcarbonyloxy, aralkycarbonyloxy, heteroaralkylcarbonyloxy, (cycloalkyl)alkylcarbonyloxy, (cycloheteroalkyl)alkylcarbonyloxy, alkylcarbonyl, arylcarbonyl, heteroarylcarbonyl, cycloalkycarbonyl, cycloheteroalkylcarbonyl, aralkycarbonyl, heteroaralkylcarbonyl, (cycloalkyl)alkylcarbonyl, (cycloheteroalkyl)alkylcarbonyl, alkylaminocarbonyl, arylaminocarbonyl, aralkylaminocarbonyl, heteroarylaminocarbonyl, heteroaralkylaminocarbonyl, alkylcarbonylamino, arylcarbonylamino, heteroarylcarbonylamino, cycloalkylcarbonylamino, cycloheteroalkylcarbonylamino, aralkylcarbonylamino, heteroar alkylcarbonylamino, (cycloalkyl)alkylcarbonylamino, (cycloheteroalkyl)alkylcarbonylamino, dialkylamino, arylamino, diarylamino, aralkylamino, diaralkylamino, heteroarylamino, diheteroarylamino, heteroaralkylamino, diheteroaralkylamino, alkylsulfonyl, arylsulfonyl, heteroarylsulfonyl, cycloalkylsulfonyl, aralkylcarbonylthioooxyl, carbonylthio, heteroaralkylcarbonylthio, (cycloalkyloxy)carbonylthio, (cycloheteroalkyl)alkylcarbonylthio, alkyloxycarbonyl, aryloxycarbonyl, heteroaryloxycarbonyl, cycloalkyloxylcarbonyl, cycloheteroalkyloxycarbonyl, aralyoxycarbonyloxloxycarbonyl, heteroaralkyloxycarbony, (cycloalkyl)alkyloxycarbonyl, (cycloheteroalkyl)alkyloxycarbonyl, iminoalkyl, iminocycloalkyl, ininocyclohetероalkyl, iminoaralkyl, iminoheteroaralkyl, (cycloalkyl)iminoalkyl, and (cycloheteroalkyl)iminoalkyl. $R^3$ and $R^6$ are selected independently from the group consisting of: oxo, thiocarbonyl, imino, optionally substituted dialkylimino, diarylimino, di-heteroarylimino, alkylarylimino, alkylheteroarylimino, arylheteroarylimino, alkyloxyalkylamino, di-(alkyloxyalkyl)amino, alkylthioalkylamino, di-(alkylthioalkyl)amino, alkylaminoalkylamino, di-(alkylaminoalkyl)amino, aryloxyalkylamino, di-(aryloxyalkyl)amino, arylthioalkylamino, di-(arylthioalkyl)amino, arylaminoalkylamino, di-(arylaminoalkyl)amino, heteroaryloxyalkylamino, di-(heteroaryloxyalkyl)amino, heteroarylthioalkylamino, di-(heteroarylthioalkyl)amino, heteroarylaminoalkylamino, and di-(heteroarylaminoalkyl)amino. However, at least one of $R^3$ and $R^6$ is selected from the group consisting of: alkyloxyalkylamino, di-(alkyloxyalkyl)amino, alkylthioalkylamino, di-(alkylthioalkyl)amino, alkylaminoalkylamino, di-(alkylaminoalkyl)amino, aryloxyalkylamino, di-(aryloxyalkyl)amino, arylthioalkylamino, di-(arylthioalkyl) amino, arylaminoalkylamino, di-(arylaminoalkyl)amino, heteroaryloxyalkylamino, di-(heteroaryloxyalkyl)amino, heteroarylthioalkylamino, di-(heteroarylthioalkyl)amino, heteroarylaminoalkylamino, and di-(heteroarylaminoalkylene)amino.

Those having ordinary skill in the art will appreciate that compounds having the structure of Compound 1 can exist in a variety of formal hybridization structures that may or may not include a formal charge; thus, the structural formula for Compound 1 shown above implicitly includes all equivalent resonance structures including any charges. Similarly, the illustration of any specific resonance structure herein is defined to include all equivalent resonance structures implicitly unless specifically noted otherwise. The identification of such resonance structures and their equivalents is well known to persons having ordinary skill in the art.

In some embodiments, the compounds of the invention have the structure shown above as Compound 1, wherein $R^3$ is selected from the group consisting of: alkyloxyalkylamino, di-(alkyloxyalkyl)amino, alkylthioalkylamino, di-(alkylthioalkyl)amino, alkylaminoalkylamino, di-(alkylaminoalkyl) amino, aryloxyalkylamino, di-(aryloxyalkyl)amino, arylthioalkylamino, di-(arylthioalkyl)amino, arylaminoalkylamino, di-(arylaminoalkylene)amino, heteroaryloxyalkylamino, di-(heteroaryloxyalkylene)amino, heteroarylthioalkylamino, di-(heteroarylthioalkyl)amino, heteroarylaminoalkylamino, and di-(heteroarylaminoalkyl)amino. More specific embodiments from among these compounds include those wherein at least one of $R^1$ and $R^8$ is selected from the group consisting of: halo, nitro, cyano, carboxyl, formyl, and optionally substituted alkyl. Still more specific embodiments are those among the foregoing in which at least one of $R^1$ and $R^8$ is selected from the group consisting of: halo, carboxyl, and optionally substituted alkyl; and, still more specifically, those compounds as just described wherein at least one of $R^1$ and $R^8$ is selected from the group consisting of: halo, carboxyl, and optionally substituted alkyl.

In other more specific embodiments, the present invention provides compounds having the structure shown and described most generally as Compound 1 above wherein at least one of $R^1$ and $R^8$ is halo, and, still more specifically, wherein least one of $R^1$ and $R^8$ is fluoro and wherein least one of $R^1$ and $R^8$ is chloro. In yet other specific embodiments $R^1$ and $R^8$ are both halo; and more specifically, $R^1$ and $R^8$ are both fluoro or $R^1$ and $R^8$ are both chloro.

Returning to Compound 1 and the general description thereof, the present invention further provides compounds wherein at least one of $R^1$ and $R^8$ is selected from the group consisting of: halo, carboxyl, and optionally substituted alkyl. Among these compounds, more specific embodiments are those wherein at least one of $R^1$ and $R^8$ is selected from the group consisting of: halo, carboxyl, and optionally substituted alkyl. Still more specific embodiments among these compounds are those in which at least one of $R^1$ and $R^8$ is halo; and more specifically at least one of $R^1$ and $R^8$ is fluoro, or at least one of $R^1$ and $R^8$ is chloro. Still other specific embodiments among those just described are those in which $R^1$ and $R^8$ are both halo; and more specifically those in which $R^1$ and $R^8$ are both fluoro or $R^1$ and $R^8$ are both chloro.

Again returning to Compound 1 and the general description thereof, the present invention further provides compounds wherein $R^6$ is selected from the group consisting of: alkyloxyalkylamino, di-(alkyloxyalkyl)amino, alkylthioalkylamino, di-(alkylthioalkyl)amino, alkylaminoalkylamino, di-(alkylaminoalkyl)amino, aryloxyalkylamino, di-(aryloxyalkyl)amino, arylthioalkylamino, di-(arylthioalkyl)amino, arylaminoalkylamino, di-(arylaminoalkylene)amino, heteroaryloxyalkylamino, di-(heteroaryloxyalkylene)amino, heteroarylthioalkylamino, di-(heteroarylthioalkyl)amino, heteroarylaminoalkylamino, and di-(heteroarylaminoalkyl)amino. Among these compounds are more specific embodiments wherein at least one of $R^1$ and $R^8$ is selected from the group consisting of: halo, nitro, cyano, carboxyl, formyl, and optionally substituted alkyl. Still more specific embodiments are those in which at least one of $R^1$ and $R^8$ is selected from the group consisting of: halo, carboxyl, and optionally substituted alkyl; and still more specific compounds are those in which at least one of $R^1$ and $R^8$ is selected from the group consisting of: halo, carboxyl, and optionally substituted alkyl. Among these compounds are those in which at least one of $R^1$ and $R^8$ is halo; and more specifically compounds in which at least one of $R^1$ and $R^8$ is fluoro or at least one of $R^1$ and $R^8$ is chloro. Other compounds from among the foregoing are those in which $R^1$ and $R^8$ are both halo; and more specifically those wherein $R^1$ and $R^8$ are both fluoro, or those wherein $R^1$ and $R^8$ are both chloro.

Yet again returning to the compounds described with respect to Compound 1, other more specific embodiments of the invention include those compounds wherein each of $R^3$ and $R^6$ is selected independently from the group consisting of: alkyloxyalkylamino, di-(alkyloxyalkyl)amino, alkylthioalkylamino, di-(alkylthioalkyl)amino, alkylaminoalkylamino, di-(alkylaminoalkyl)amino, aryloxyalkylamino, di-(aryloxyalkyl)amino, arylthioalkylamino, di-(arylthioalkyl)amino, arylaminoalkylamino, di-(arylaminoalkylene)amino, heteroaryloxyalkylamino, di-(heteroaryloxyalkylene)amino, heteroarylthioalkylamino, di-(heteroarylthioalkyl)amino, heteroarylaminoalkylamino, and di-(heteroarylaminoalkyl)amino. More specific embodiments of the invention are compounds among the foregoing wherein at least one of $R^1$ and $R^8$ is selected from the group consisting of: halo, nitro, cyano, carboxyl, formyl, and optionally substituted alkyl. Still more specific embodiments are those in which at least one of $R^1$ and $R^8$ is selected from the group consisting of: halo, carboxyl, and optionally substituted alkyl; and still more specific compounds are those in which at least one of $R^1$ and $R^8$ is selected from the group consisting of: halo, carboxyl, and optionally substituted alkyl. Among these compounds are those in which at least one of $R^1$ and $R^8$ is halo; and more specifically compounds in which at least one of $R^1$ and $R^8$ is fluoro or at least one of $R^1$ and $R^8$ is chloro. Other compounds from among the foregoing are those in which $R^1$ and $R^8$ are both halo; and more specifically those wherein $R^1$ and $R^8$ are both fluoro, or those wherein $R^1$ and $R^8$ are both chloro.

Still again returning to the compounds described above with respect to Compound 1, the present invention also provides more specific embodiments in which one of $R^3$ and $R^6$ is selected from the group consisting of: oxo, thiocarbonyl, imino, optionally substituted dialkylimino, diarylimino, diheteroarylimino, alkylarylimino, alkylheteroarylimino, arylheteroarylimino. More particular compounds of the invention are those in which one of $R^3$ and $R^6$ is oxo. In more particular embodiments, the compounds of the invention include those having the substituents just described and further wherein at least one of $R^1$ and $R^8$ is selected from the group consisting of: halo, nitro, cyano, carboxyl, formyl, and optionally substituted alkyl; still more particularly wherein at least one of $R^1$ and $R^8$ is selected from the group consisting of: halo, carboxyl, and optionally substituted alkyl; and yet more particularly wherein at least one of $R^1$ and $R^8$ is selected from the group consisting of: halo, carboxyl, and optionally substituted alkyl. Still more specific embodiments are those in which at least one of $R^1$ and $R^8$ is selected from the group consisting of: halo, carboxyl, and optionally substituted alkyl; and still more specific compounds are those in which at least one of $R^1$ and $R^8$ is selected from the group consisting of: halo, carboxyl, and optionally substituted alkyl. Among these compounds are those in which at least one of $R^1$ and $R^8$ is halo; and more specifically compounds in which at least one of $R^1$ and $R^8$ is fluoro or at least one of $R^1$ and $R^8$ is chloro. Other compounds from among the foregoing are those in which $R^1$ and $R^8$ are both halo; and more specifically those wherein $R^1$ and $R^8$ are both fluoro, or those wherein $R^1$ and $R^8$ are both chloro.

Again returning to the compounds described above under the generic structure of Compound 1, in other embodiments the present invention includes those compounds wherein $R^3$ and $R^6$ are selected independently from the group consisting of: alkyloxyethyleneamino, di-(alkyloxyethylene)amino, alkylthioethyleneamino, di-(alkylthioethylene)amino, alkylaminoethyleneamino, di-(alkylaminoethylene)amino, aryloxyethyleneamino, di-(aryloxyethylene)amino, arylthioethyleneamino, di-(arylthioethylene)amino, arylaminoethyleneamino, di-(arylaminoethylene)amino, heteroaryloxyethyleneamino, di-(heteroaryloxyethylene)amino, heteroarylthioethyleneamino, di-(heteroarylthioethylene)amino, heteroarylaminoethyleneamino, and di-(heteroarylaminoethylene)amino. In more specific embodiments, $R^3$ and $R^6$ are selected independently from the group consisting of: alkyloxyethyleneamino, di-(alkyloxyethylene)amino, alkylthioethyleneamino, di-(alkylthioethylene)amino, alkylaminoethyleneamino, di-(alkylaminoethylene)amino. In still more specific embodiments, $R^3$ and $R^6$ are selected independently from the group consisting of: methyloxyethyleneamino, di-(methyloxyethylene)amino, methylthioethyleneamino, di-(methylthioethylene)amino, methylaminoethyleneamino, di-(methylaminoethylene)amino. More specific embodiments are those in which at least one of $R^3$ and $R^6$ is methyloxyethyleneamino.

Among those embodiments just described in which at least one of $R^3$ and $R^6$ is methyloxyethyleneamino, more specific embodiments are those wherein at least one of $R^1$ and $R^8$ is selected from the group consisting of: halo, nitro, cyano, carboxyl, formyl, and optionally substituted alkyl; and more particularly wherein at least one of $R^1$ and $R^8$ is selected from the group consisting of: halo, carboxyl, and optionally substituted alkyl. Still more specific embodiments are those in which at least one of $R^1$ and $R^8$ is selected from the group consisting of: halo, carboxyl, and optionally substituted alkyl; and still more specific compounds are those in which at least one of $R^1$ and $R^8$ is selected from the group consisting of: halo, carboxyl, and optionally substituted alkyl. Among these compounds are those in which at least one of $R^1$ and $R^8$ is halo; and more specifically compounds in which at least one of $R^1$ and $R^8$ is fluoro or at least one of $R^1$ and $R^8$ is chloro. Other compounds from among the foregoing are those in which $R^1$ and $R^8$ are both halo; and more specifically those wherein $R^1$ and $R^8$ are both fluoro, or those wherein $R^1$ and $R^8$ are both chloro.

In other embodiments, one of $R^3$ and $R^6$ is methyloxyethyleneamino and the other of $R^3$ and $R^6$ is selected from the group consisting of: oxo, thiocarbonyl, imino, optionally substituted dialkylimino, diarylimino, di-heteroarylimino, alkylarylimino, alkylheteroarylimino, arylheteroarylimino. More particular embodiments are those wherein one of $R^3$ and $R^6$ is methyloxyethyleneamino and the other one of $R^3$ and $R^6$ is oxo. Among these compounds are still more particular embodiments in which at least one of $R^1$ and $R^8$ is selected from the group consisting of: halo, nitro, cyano, carboxyl, formyl, and optionally substituted alkyl; more particularly wherein at least one of $R^1$ and $R^8$ is selected from the group consisting of: halo, carboxyl, and optionally substituted alkyl; and still more particularly wherein at least one of $R^1$ and $R^8$ is selected from the group consisting of: halo, carboxyl, and optionally substituted alkyl. Still more specific embodiments are those in which at least one of $R^1$ and $R^8$ is selected from the group consisting of: halo, carboxyl, and optionally substituted alkyl; and still more specific compounds are those in which at least one of $R^1$ and $R^8$ is selected from the group consisting of: halo, carboxyl, and optionally substituted alkyl. Among these compounds are those in which at least one of $R^1$ and $R^8$ is halo; and more specifically compounds in which at least one of $R^1$ and $R^8$ is fluoro or at least one of $R^1$ and $R^8$ is chloro. Other compounds from among the foregoing are those in which $R^1$ and $R^8$ are both halo; and more specifically those wherein $R^1$ and $R^8$ are both fluoro, or those wherein $R^1$ and $R^8$ are both chloro.

In another aspect, the present invention provides methods for treating a viral disease in a mammal afflicted with such disease, comprising administering to such mammal a therapeutically effective amount of a compound among those described above with respect to Compound 1. In more particular embodiments the viral disease is Ebola virus. In other more particular embodiments, the viral disease is Marburg virus, Those having ordinary skill in the art will understand how to formulate and administer the compounds described herein.

4.3 Synthesis of the Compounds of the Invention

The compounds of the present invention can be synthesized using techniques and materials known to those of skill in the art. Starting materials for the compounds of the invention may be obtained using standard techniques and commercially available precursor materials, such as those available from Aldrich Chemical Co. (Milwaukee, Wis.), Sigma Chemical Co. (St. Louis, Mo.), Lancaster Synthesis (Windham, N.H.), Apin Chemicals, Ltd. (New Brunswick, N.J.), Ryan Scientific (Columbia, S.C.), Maybridge (Cornwall, England), Arcos (Pittsburgh, Pa.), and Trans World Chemicals (Rockville, Md.)

The procedures described herein for synthesizing the compounds of the invention may include one or more steps of protection and deprotection (e.g., the formation and removal of acetal groups). In addition, the synthetic procedures disclosed below can include various purifications, such as column chromatography, flash chromatography, thin-layer chromatography ("TLC"), recrystallization, distillation, high-pressure liquid chromatography ("HPLC") and the like. Also, various techniques well known in the chemical arts for the identification and quantification of chemical reaction products, such as proton and carbon-13 nuclear magnetic resonance ($^1$H and $^{13}$C NMR), infrared and ultraviolet spectroscopy ("IR" and "UV"), X-ray crystallography, elemental analysis ("EA"). HPLC and mass spectroscopy ("MS") can be used for identification, quantitation and purification as well.

Although the schemes below illustrate specific starting materials and products, those having ordinary skill in the art will understand that many substitution patterns can be made using known methods and materials in combination with the teachings herein.

Symmetrical compounds of the invention can be made using the transformations described in the following scheme:

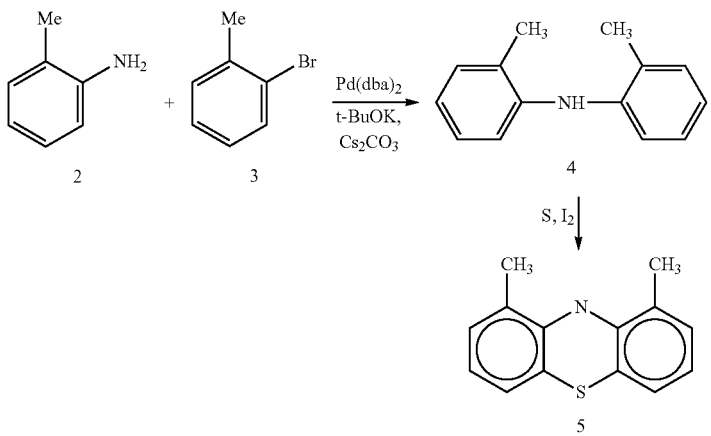

Starting from commercially available methylaniline (2) and bromotoluene (3), reaction with tris(dibenzylideneacetone)dipalladium(0), Pd(dba)$_2$ (or Pd$_2$(dba)$_3$), in suitable basic conditions, the coupled secondary amine 4. Subsequent reaction of that product with elemental sulfur and iodine provides the symmetrically substituted phenothiazine 5. Symmetrical bromination is achieved by reaction of 5 with bromine and acetic acis (below).

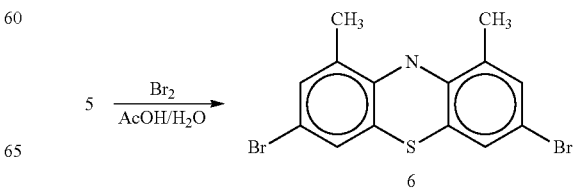

Reaction of the di-bromide with HN((CH$_2$)$_2$OCH$_3$)$_2$ in chloroform at room temperature provides the desired symmetrical amine 7 (R=(CH$_2$)$_2$OCH$_3$) illustrated below. The specific details of these reactions can be found in Example 1 further hereinbelow.

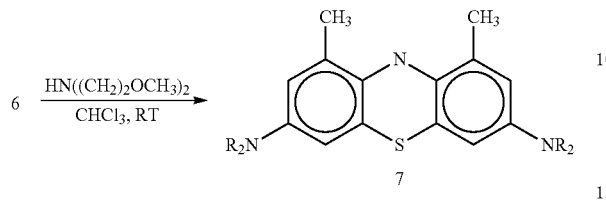

Asymmetrical substitution patterns can be made using the scheme below.

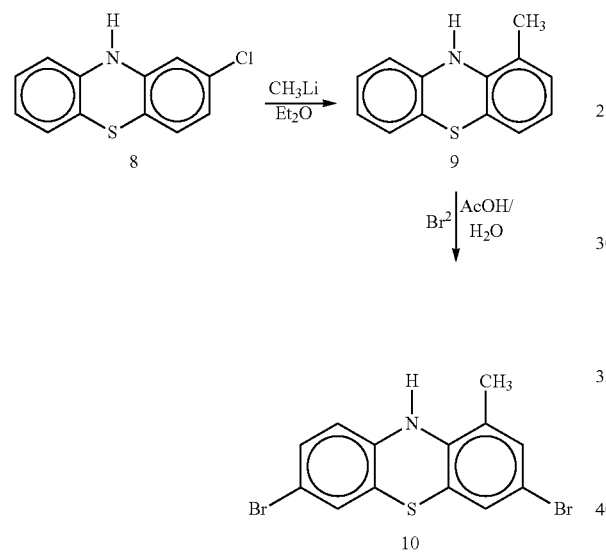

Starting from 2-chlorodiphenylthiazine (8), formation of the 1-methyl analog (9) is achieved reaction by reaction with methyllithium in diethylether. Reaction of that product with bromine in acetic acid and water provides the di-bromo adduct (10).

Reaction of the di-bromide with HN((CH$_2$)$_2$OCH$_3$)$_2$ in chloroform at room temperature provides the desired 3,7-diamine 11 (R=(CH$_2$)$_2$OCH$_3$) illustrated below. The specific details of these reactions can be found in Example 1 further hereinbelow.

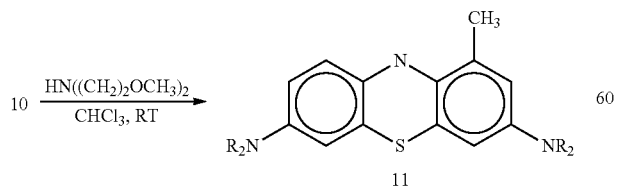

Routes to asymmetrical substitutions at the 3-and 7-positions can be made using the following scheme:

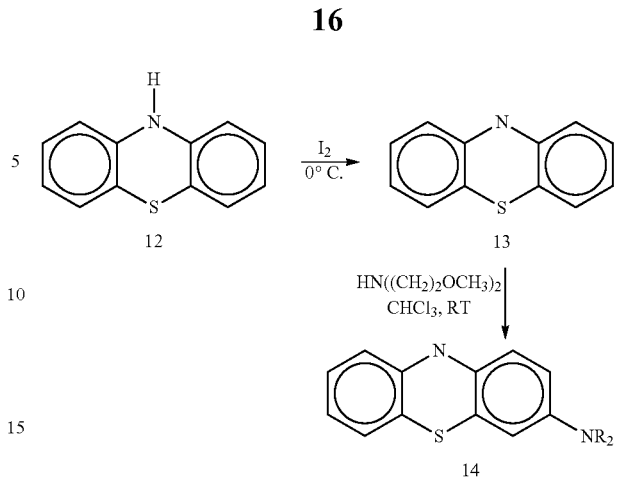

Reaction of 13 with HN((CH$_2$)$_2$OCH$_3$)$_2$ in chloroform at room temperature provides the desired amine 14 (R=(CH$_2$)$_2$OCH$_3$).

Reaction of 14 with pyrrolidine and cesium carbonate (Cs$_2$CO$_3$) in dimethyl—formamide at room temperature provides the desired asymmetical diamine 15

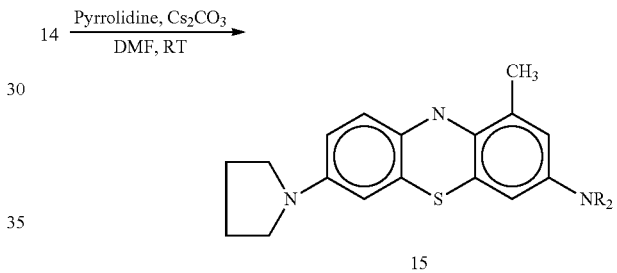

The specific details of these reactions can be found in Example 10 further hereinbelow.

Another route to symmetrical amine substitutions is provided here:

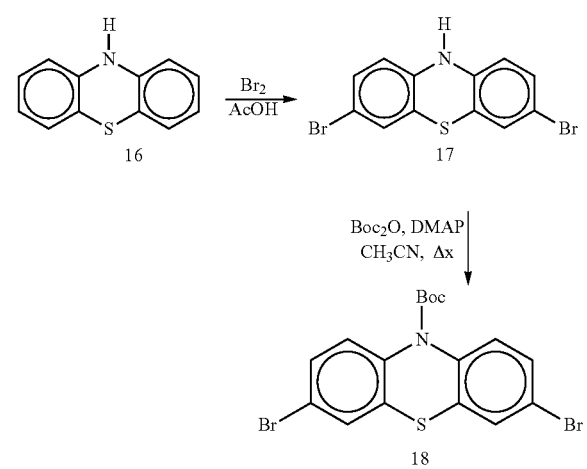

Reaction of 16 with bromine in acetic acid provides the desired dibromide 17. Further reaction with Boc$_2$O and DMAP in acetonitrile with heating provides the protected analog 18.

Reaction of 18 with pyrrolidine and cesium carbonate ($Cs_2CO_3$) in dimethyl—formamide at room temperature provides the desired symmetrical diamine 19

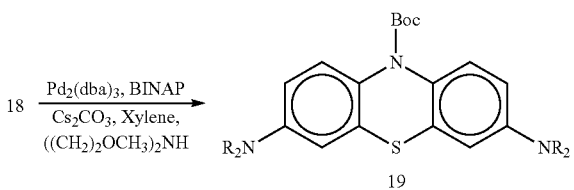

Reaction of 19 with TFA and methylene chloride at 70° C. provides the desired product 20 (R=$(CH_2)_2OCH_3$).

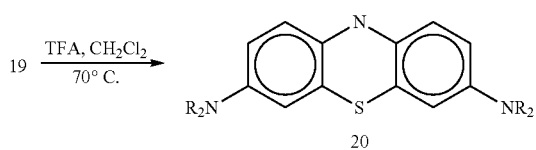

The specific details of these reactions can be found in Example 20 further hereinbelow.

Compounds having an oxo substituent on the ring at $R^3$ or $R^6$ can be made using the following scheme:

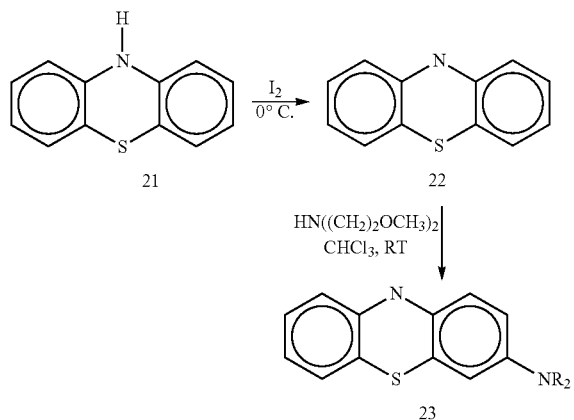

Starting from 21 as described earlier, reaction with iodine at 0° C. provides 22. Reaction of 22 with $HN((CH_2)_2OCH_3)_2$ in chloroform at room temperature provides the desired amine 23 (R=$(CH_2)_2OCH_3$) illustrated above.

Reaction of 23 with 8 M KOH in dioxane at room temperature provides the desired asymmetical diamine 24

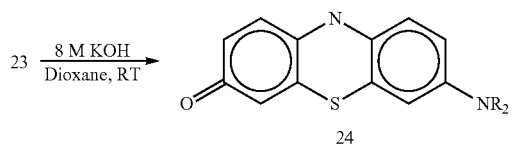

The specific details of these reactions can be found in Example 25 further hereinbelow.

4.4 Compositions for, and Methods of, Treating Viral Infections

Compounds of the present invention can be administered in a variety of ways including enteral, parenteral and topical routes of administration. For example, suitable modes of administration include oral, subcutaneous, transdermal, transmucosal, iontophoretic, intravenous, intramuscular, intraperitoneal, intranasal, subdural, rectal, vaginal, and the like.

In accordance with other embodiments of the present invention, there is provided a composition comprising a compound described here, together with a pharmaceutically acceptable carrier or excipient. Suitable pharmaceutically acceptable excipients include processing agents and drug delivery modifiers and enhancers, such as, for example, calcium phosphate, magnesium stearate, talc, monosaccharides, disaccharides, starch, gelatin, cellulose, methyl cellulose, sodium carboxymethyl cellulose, dextrose, hydroxypropyl-β-cyclodextrin, polyvinylpyrrolidinone, low melting waxes, ion exchange resins, and the like, as well as combinations of any two or more thereof. Other suitable pharmaceutically acceptable excipients are described in REMINGTON'S PHARMACEUTICAL SCIENCES, Mack Pub. Co., New Jersey (1991), which is incorporated herein by reference.

Pharmaceutical compositions of the present invention may be in any form suitable for the intended method of administration, including, for example, a solution, a suspension, or an emulsion. Liquid carriers are typically used in preparing solutions, suspensions, and emulsions. Liquid carriers contemplated for use in the practice of the present invention include, for example, water, saline, pharmaceutically acceptable organic solvent(s), pharmaceutically acceptable oils or fats, and the like, as well as mixtures of two or more thereof. The liquid carrier may contain other suitable pharmaceutically acceptable additives such as solubilizers, emulsifiers, nutrients, buffers, preservatives, suspending agents, thickening agents, viscosity regulators, stabilizers, and the like. Suitable organic solvents include, for example, monohydric alcohols, such as ethanol, and polyhydric alcohols, such as glycols. Suitable oils include, for example, soybean oil, coconut oil, olive oil, safflower oil, cottonseed oil, and the like. For parenteral administration, the carrier can also be an oily ester such as ethyl oleate, isopropyl myristate, and the like. Compositions of the present invention may also be in the form of microparticles, microcapsules, liposomal encapsulates, and the like, as well as combinations of any two or more thereof.

The compounds of the present invention may be administered orally, parenterally, sublingually, by inhalation spray, rectally, vaginally, or topically in dosage unit formulations containing conventional nontoxic pharmaceutically acceptable carriers, adjuvants, and vehicles as desired. Topical administration may also involve the use of transdermal administration such as transdermal patches or ionophoresis devices. The term parenteral as used herein includes subcutaneous injections, intravenous, intramuscular, intrasternal injection, or infusion techniques.

Injectable preparations, for example, sterile injectable aqueous or oleaginous suspensions may be formulated according to the known art using suitable dispersing or wetting agents and suspending agents. The sterile injectable preparation may also be a sterile injectable solution or suspension in a nontoxic parenterally acceptable diluent or solvent, for example, as a solution in 1,3-propanediol. Among the acceptable vehicles and solvents that may be employed are water, Ringer's solution, and isotonic sodium chloride solution. In addition, sterile, fixed oils are conventionally employed as a solvent or suspending medium. For this purpose, any bland fixed oil may be employed including synthetic mono- or diglycerides. In addition, fatty acids such as oleic acid can be useful in the preparation of injectables.

Suppositories for rectal or vaginal administration of the drug can be prepared by mixing the drug with a suitable nonirritating excipient such as cocoa butter and polyethylene glycols that are solid at ordinary temperatures but liquid at the rectal temperature and will therefore melt in the rectum and release the drug.

Solid dosage forms for oral administration may include capsules, tablets, pills, powders, and granules. In such solid dosage forms, the active compound may be admixed with at least one inert diluent such as sucrose lactose or starch. Such dosage forms may also comprise, as is normal practice, additional substances other than inert diluents, e.g., lubricating agents such as magnesium stearate. In the case of capsules, tablets, and pills, the dosage forms may also comprise buffering agents. Tablets and pills can additionally be prepared with enteric coatings.

Liquid dosage forms for oral administration may include pharmaceutically acceptable emulsions, solutions, suspensions, syrups, and elixirs containing inert diluents commonly used in the art, such as water. Such compositions may also comprise adjuvants, such as wetting agents, emulsifying and suspending agents, cyclodextrins, and sweetening, flavoring, and perfuming agents.

The compounds of the present invention can also be administered in the form of liposomes. As is known in the art, liposomes are generally derived from phospholipids or other lipid substances. Liposomes are formed by mono- or multi-lamellar hydrated liquid crystals that are dispersed in an aqueous medium. Any non-toxic, physiologically acceptable and metabolizable lipid capable of forming liposomes can be used. The present compositions in liposome form can contain, in addition to a compound of the present invention, stabilizers, preservatives, excipients, and the like. The preferred lipids are the phospholipids and phosphatidyl cholines (lecithins), both natural and synthetic. Methods to form liposomes are known in the art.

While the compounds of the invention can be administered as the sole active pharmaceutical agent, they can also be used in combination with one or more other compound as described herein, or in combination with other agents used in the treatment or prevention of AD and related diseases, or both.

In addition, the compounds of the present invention can be used, either singly or in combination as described above, in combination with other modalities for preventing or treating AD and related diseases or disorders. Such other treatment modalities include without limitation, surgery, radiation, hormone supplementation, and diet regulation. These can be performed sequentially (e.g., treatment with a compound of the invention following surgery or radiation) or in combination (e.g., in addition to a diet regimen).

The additional active agents may generally be employed in therapeutic amounts as indicated by sources well known to those having ordinary skill in the art, e.g., the PHYSICIAN'S DESK REFERENCE (PDR) 53$^{rd}$ Edition (1999), which is incorporated herein by reference, or such therapeutically useful amounts as would be known to one of ordinary skill in the art. The compounds of the invention and the other therapeutically active agents can be administered at the recommended maximum clinical dosage or at lower doses. Dosage levels of the active compounds in the compositions of the invention may be varied to obtain a desired therapeutic response depending on the route of administration, severity of the disease and the response of the patient. The combination can be administered as separate compositions or as a single dosage form containing both agents. When administered as a combination, the therapeutic agents can be formulated as separate compositions that are given at the same time or different times, or the therapeutic agents can be given as a single composition.

In accordance with yet other embodiments, the present invention provides methods for treating or preventing viral infections or similar disorder in a human or animal subject in which an amount of a compound of the invention that is effective to at least ameliorate disease symptoms. Effective amounts of the compounds of the invention generally include any amount sufficient to detectably modulate viral activity using standard measures, by other methods known to those having ordinary skill in the art, or by detecting prevention or alleviation of symptoms in a subject afflicted with a virus.

The amount of active ingredient that may be combined with the carrier materials to produce a single dosage form will vary depending upon the host treated and the particular mode of administration. It will be understood, however, that the specific dose level for any particular patient will depend upon a variety of factors including the activity of the specific compound employed, the age, body weight, general health, sex, diet, time of administration, route of administration, rate of excretion, drug combination, and the severity of the particular disease undergoing therapy. The prophylactically or therapeutically effective amount for a given situation can be readily determined by routine experimentation and is within the skill and judgment of the ordinary clinician.

For exemplary purposes of the present invention, a prophylactically or therapeutically effective dose will generally be from about 0.1 mg kg$^{-1}$ d$^{-1}$ to about 100 mg kg$^{-1}$ d$^{-1}$, preferably from about 1 mg kg$^{-1}$ d$^{-1}$ to about 20 mg kg$^{-1}$ d$^{-1}$, and most preferably from about 10 mg kg$^{-1}$ d$^{-1}$ to about 10 mg kg$^{-1}$ d$^{-1}$ of a compound of the present invention, which may be administered in one or multiple doses.

4.5 Examples

The following Examples are provided to illustrate certain aspects of the present invention and to aid those of skill in the art in the art in practicing the invention. These Examples are in no way to be considered to limit the scope of the invention in any manner.

4.5.1 Example 1

3,7-bis(bis(2-methoxyethyl)amino)-1,9-dimethylphenothiazin-5-ium bromide

All glassware was heated under argon atmosphere and then allowed to cool to room.

4.5.1.1 Example 1A

Synthesis of Di(2-tolyl)amine

The following were added to a reaction vessel dried as indicated: One mole percent of Pd$_2$(dba)$_3$ (1.39 g, 1.52 mmol) or Pd(dba)$_2$ (1.38 g, 2.4 mmol, 1.4 mol %), 2-(di-tert-butylphosphino)biphenyl (1.09 g, 3.65 mmoles, 2.4 mole %), 2-bromotoluene (40 mL, 332.1 mmol) or 2-chlorotoluene (39 mL, 332.1 mmol), lithium amide (3.47 g, 151.1 mmol, 45 mol %), sodium t-butoxide 29.5 g, 297.7 mmol, 90 mol %), and then toluene (150 mL). The mixture was then heated at 80° C. under argon overnight. Following the reaction period the mixture was allowed to cool to room temperature, and then diluted with diethyl ether and filtered through a pad of celite. The collected filtrate was concentrated in vacuo. Purify of the resulting residue was accomplished by flash silica gel chromatography in hexane to give the desired product as white crystals with a yellow tint (23.4 g, 118.6 mmol, 72% yield).

Alternatively, purification was performed by repeated crystallizations of the residue from hot isopropanol or acetone/isopropanol to obtain the desired product. Another alternative purification was accomplished by dissolving the residue in dichloromethane and passing the mixture through a silica plug with hexane rinses, followed by hexane containing about 1% dichloromethane; the filtrates were collected and concentrated to obtain yellow-white solids as the desired product.

4.5.1.2 Example 1B

Cyclization of di(2-tolyl)amine to 1,9-dimethylphenothiazine

Di(2-tolyl)amine (11.7 g, 59.3 mmol) was introduced into a 3-neck 100 mL round-bottom flask. Elemental sulfur (3.9 g, 121.65 mmol, two equivalent), crushed iodine (0.44 g, 1.73 mmol, 3 mole %), and then o-dichlorobenzene (22 mL) was added next, along with an outlet to a dilute bleach solution (for hydrogen sulfide evolution), under argon atmosphere. The reaction mixture was heated at reflux at 180° C. for 4 hours, after which the solvent was removed under reduced pressure. Purification was performed by Isco column chromatography using 2% ethyl acetate/98% hexane. The desired product was obtained as white crystals (2 g, 8.8 mmol, 15% yield).

Alternatively, di(2-tolyl)amine (8.9525 g, 45.3 mmol) was introduced into a round-bottom flask. Elemental sulfur (2.98 g, 92.9 mmol, two equivalents) then crushed iodine (3.28 g, 12.9 mmol, 28 mole %) were then added, and an outlet to a dilute bleach solution (for hydrogen sulfide) was attached, and the vessel contents were then put under argon. The mixture was stirred at 210° C. for 30 minutes or until no starting material was present by LC/MS. Upon completion, the reaction was cooled to about 60° C., and then hot hexane was added for extraction. The hot hexane extractions were repeated about four times, and the extractions were combined and concentrated in vacuo. The resulting residue was purified either through repeated hot acetone/isopropanol crystallizations or Isco column chromatography using 2% ethyl acetate/98% hexane to obtain product as white crystals (2.92 g, 12.8 mmol, 28% yield).

4.5.1.3 Example 1C

Synthesis of 3,7-dibromo-1,9-dimethylphenothiazin-5-ium bromide

Dimethylphenothiazine (400 mg, 1.75 mmol) was put in a flask, and suspended in acetic acid (21 mL), after which a solution of bromine (20 eq.) in acetic acid (18 mL solution, 10% v/v, 38.8 mmol bromine) was added, and the solution stirred for two minutes. Deionized water (70 mL) was added; and the resulting brown precipitate was filtered off, rinsed with diethyl ether, and then stirred in diethyl ether (80 mL) for an hour. The precipitate was filtered off again and then stirred with diethyl ether (80 mL) for another hour, after which the precipitate filtered again and then pumped under house vacuum overnight to dry. A brown precipitate was obtained (900 mg) and used in the next reaction without purification.

4.5.1.4 Example 1D

Addition of dimethoxydiethylamine to 3,7-dibromo-1,9-dimethylphenothiazin-5-ium bromide Phenothiazinium bromide (812 mg, 1.75 mmol) was put in a flask with dichloromethane or chloroform (190 mL). The reaction mixture was put under an argon balloon, and then dimethoxydiethylamine (1.3 mL, 8.7 mmol) was injected over a minute period. The reaction mixture was stirred for four hours, after which, the solvent was removed under vacuum. The remainder was dissolved in dichloromethane and extracted with 1% v/v aqueous hydrogen bromide (58 mL) once, and then the organic layer was extracted with deionized water twice (until organic layer was pH-neutral). The organic layer was dried over sodium sulfate, which was removed under vacuum. Purification was performed using Isco column chromatography (methanol/dichloromethane) to obtain a dark blue solid as product (124 mg, 0.218 mmol, 12% yield).

4.5.2 Example 2

3,7-bis(bis(2-methoxyethyl)amino)-1,9-dimethoxyphenothiazin-5-ium bromide

The synthesis was carried out as in Example 1 above.

4.5.3 Example 3

3,7-bis(bis(2-methoxyethyl)amino)-1,9-diisopropylphenothiazin-5-ium bromide

The synthesis was carried out as in Example 1 above.

4.5.4 Example 4

3,7-bis(bis(2-methoxyethyl)amino)-1-methylphenothiazin-5-ium bromide 4.5.4.1 Synthesis of 1-methyl-10H-phenothiazine To a solution of 2-chlorophenothiazine (4.67 g, 0.020 mole) in anhydrous ethyl ether (60 mL) methyl lithium ($R=CH_3$ in product) (1.6 M solution, 62.5 mL, 0.1 mol) was added at room temperature (1 h). After the mixture had been stirred for 6 h, ice water was added slowly (30 min) and after that the stirring was continued for 30 min. The organic layer was separated and combined with ether extracts of the aqueous phase. The combined organic phase was washed with water, dried ($Na_2SO_4$) and concentrated to give the crude product (1.58 g, 37% yield). The desired final product was purified by flash chromatography.

4.5.4.2 Synthesis of 3,7-dibromo-1-methylphenothiazin-5-ium bromide

1-Methylphenothiazine (0.85 g, 0.004 mol) was dissolved in oxygen-free acetic acid (40 mL) and a solution of bromine also in acetic acid (4.3 mL $Br_2$ in 40 mL AcOH) was added to it all at once with vigorousstirring. Stirring was continued for about 1-2 min. Water (100 mL) was then added to mixture; and the subsequent dark red precipitate was filtered off, washed with ether and dried under vacuum (1.7 g, 95% yield). The product was used for next step without further purification.

4.5.4.3 Synthesis of 3,7-bis(bis(2-methoxyethyl) amino)-1-methylphenothiazin-5-ium bromide To a solution of 1-methyl-3,7-dibromophenothiazinium bromide (315 mg, 0.7 mmol) in chloroform (15 mL) kept under argon, bis(2-methoxyethyl)amine (0.52 mL, 3.5 mmol) was added (30 min) with vigorous stirring. The mixture was stirred for 3 h and after that extracted once with aqueous HBr (30 mL, 1% v/v) and then twice with water. The organic layer was dried ($Na_2SO_4$), concentrated and dried under vacuum (93 mg, 24% yield). The desired final product was purified by flash chromatography.

4.5.5 Example 5

3,7-bis(bis(2-methoxyethyl)amino)-1-isopropylphenothiazin-5-ium bromide

The synthesis was carried out as described in Example 4 above.

4.5.6 Example 6

3,7-bis(bis(2-methoxyethyl)amino)-1-tert-butylphenothiazin-5-ium bromide

The synthesis was carried out as described in Example 4 above.

4.5.7 Example 7

3,7-bis(bis(2-methoxyethyl)amino)-1-butylphenothiazin-5-ium bromide

The synthesis was carried out as described in Example 4 above.

4.5.8 Example 8

3,7-bis(bis(2-methoxyethyl)amino)-1-(trifluoromethyl)phenothiazin-5-ium bromide

The synthesis was carried out as described in Example 1 above.

4.5.9 Example 9

3,7-bis(bis(2-methoxyethyl)amino)-2-methoxyphenothiazin-5-ium bromide

The synthesis was carried out as described in Example 1 above.

4.5.10 Example 10

3-(Bis(2-methoxyethyl)amino)-7-(pyrrolidin-1-yl) phenothiazin-5-ium iodide

4.5.10.1 Synthesis of 1,9-diethylphenothiazin-5-ium tetraiodide hydrate

Phenothiazine (566 mg, 2.84 mmol) was dissolved in $CHCl_3$ (20 mL) and cooled to 5° C. To this solution was added a solution of 12 (2.16 g, 8.51 mmol) dissolved in $CHCl_3$ (50 mL) was added over the course of 1 h. The reaction was stirred for 1 h more at 5° C. and a dark solid precipitated. The solid was stirred in ethyl ether for 1 h and filtered. The solid was dried under vacuum to give a quantitative yield of 2.00 g.

4.5.10.2 Synthesis of 3-(bis(2-methoxyethyl)amino)-1,9-diethylphenothiazin-5-ium triiodide The phenothiazin-5-ium 1.65 g, 2.34 mmol) was dissolved in $CHCl_3$ and pyrrolidine (0.39 mL, 4.67 mmol) was added dropwise. The mixture was stirred at RT for 48 h. The solvent was decanted (or evaporated) and the solid was washed three times with ethyl ether. The crude material was used without purification.

4.5.10.3 Synthesis of 3-(bis(2-methoxyethyl)amino)-7-(pyrrolidin-1-yl)phenothiazin-5-ium iodide The 3-aminophenothiazin-5-ium triiodide was dissolved in DMF (40 mL) and $Cs_2CO_3$ was added followed by pyrrolidine (3 mL, 3 mmol). The resulting reaction mixture was stirred rapidly at room temperature for 48 h. The solvent was evaporated and the residue was dissolved in a 3:1 mixture of $CHCl_3$/MeOH. The mixture was filtered and the solvent evaporated to give a residue, which was purified by flash silica gel chromatography to give a dark solid.

4.5.11 Example 11

3,7-bis(bis(2-methoxyethyl)amino)-1,9-diethylphenothiazin-5-ium iodide

The synthesis was performed as described in Example 10.

4.5.12 Example 12

3-(bis(2-methoxyethyl)amino)-7-(4-(tert-butoxycarbonyl)piperazin-1-yl)phenothiazin-5-ium iodide The synthesis was performed as described in Example 10.

4.5.13 Example 13

3-(bis(2-methoxyethyl)amino)-7-(piperazin-1-yl) phenothiazin-5-ium 2,2,2-trifluoroacetate The material from Example 12 was dissolved in $CH_2Cl_2$ and trifluoroacetic acid (1:1) and warmed to 65° C. for 16 h. The mixture was allowed to cool to RT and the solvent was evaporated. The residue was purified with flash silica gel chromatography with $CHCl_3$/MeOH.

4.5.14 Example 14

7-(bis(2-methoxyethyl)amino)-3-(4-(tert-butoxycarbonyl)piperazin-1-yl)-1-ethylphenothiazin-5-ium iodide The synthesis was carried out as described in Example 10 above.

4.5.15 Example 15

3-(bis(2-methoxyethyl)amino)-7-(4-(tert-butoxycarbonyl)piperazin-1-yl)-1-ethylphenothiazin-5-ium iodide The synthesis was carried out as described in Example 10 above.

4.5.16 Example 16

7-(bis(2-methoxyethyl)amino)-3-(piperazin-1-yl)-2-(trifluoromethyl)phenothiazin-5-ium 2,2,2-trifluoroacetate The synthesis was carried out as described in Example 10 above.

4.5.17 Example 17

3-(bis(2-methoxyethyl)amino)-7-(piperazin-1-yl)-2-(trifluoromethyl)phenothiazin-5-ium 2,2,2-trifluoroacetate The synthesis was carried out as described in Example 10 above.

4.5.18 Example 18

3-(bis(2-methoxyethyl)amino)-7-(dimethylamino)-1-(trifluoromethyl)phenothiazin-5-ium iodide The synthesis was carried out as described in Example 10 above.

4.5.19 Example 19

3,7-bis(bis(2-methoxyethyl)amino)-1-cyanophenothiazin-5-ium iodide

The synthesis was carried out as described in Example 10 above.

4.5.20 Example 20

3,7-bis(bis(2-methoxyethyl)amino)phenothiazin-5-ium 2,2,2-trifluoroacetate

4.5.20.1 Synthesis of 3,7-Dibromo-10H-phenothiazine

Phenothiazine (5.00 g, 25.1 mmol) was suspended in glacial AcOH (180 mL) and stirred at RT. To This mixture was added $Br_2$ (33 mL, 63 mmol) in AcOH (20 mL). The mixture became very thick, but slowly began to stir again. The dark mixture was stirred for 16 h overnight. To the mixture was added $Na_2SO_3$ (6.3 g, 50 mmol) and $H_2O$ (1 mL-2 mL) was added. After stirring for 3 h at RT, an ice cold solution of NaOH (4.1 g) in $H_2O$ (400 mL). A green precipitate formed and the mixture was stirred for an additional 10 minutes. The solid was collected and dried under vacuum. The product was purified by recrystallization from i-PrOH to give 5.5 g, for a 61% yield.

4.5.20.2 Synthesis of tert-Butyl 3,7-dibromo-10H-phenothiazine-10-carboxylate A mixture of the 3,7-dibromophenothiazine (0.25 g, 0.70 mmol), Boc anhydride (0.20 g, 0.96 mmol), DMAP (8 g, 0.07 mmol) in $CH_3CN$ (5 millilter) was stirred at RT. The color of the solution became light yellow and the starting material was consumed. After one hour, a white precipitate formed which was filtered and dried under vacuum to give a quantitative yield.

4.5.20.3 Synthesis of tert-butyl 3,7-diamino-10H-phenothiazine-10-carboxylate The N-Boc-3,7-dibromophenothiazine (200 g, 0.438 mmol) was combined with $Pd(dba)_2$ (12 g, 0.021 mmol), sodium tert-butoxide (138 g, 1.44 mmol), tri-(tert-butylphosphine) (3.2 g, 0.016 mmol) and bis-(2-methoxyethyl)amine (0.13 mL, 0.89 mmol) in toluene (5 mL) and heated to reflux for 16 h. The reaction mixture as allowed to cool to room temperature and the solvent was evaporated to give a residue. The residue was partitioned between EtOAc and brine. The combined organic layers were dried over $MgSO_4$, filtered and evaporated to give a residue. The residue was used in the next step without purification.

4.5.20.4 Synthesis of 3,7-bis(bis(2-methoxyethyl)amino)phenothiazin-5-ium 2,2,2-trifluoroacetate The crude material from the reaction above was dissolved in $CH_2Cl_2$ (3 mL) and TFA (3 mL) and heated to 70° C. for 16 h. The reaction was allowed to cool to RT and the solvent was evaporated to dryness. The reaction mixture was purified by silica gel chromatography to give 35 mg of the desired product.

4.5.21 Example 21

3,7-bis(bis(2-methoxyethyl)amino)-1,9-dichlorophenothiazin-5-ium 2,2,2-trifluoroacetate The synthesis was carried out as described in Example 20 above.

4.5.22 Example 22

3,7-bis(bis(2-methoxyethyl)amino)-1-chlorophenothiazin-5-ium 2,2,2-trifluoroacetate The synthesis was carried out as described in Example 20 above.

4.5.23 Example 23

3-(bis(2-methoxyethyl)amino)-1,9-dichloro-7-(piperazin-1-yl)phenothiazin-5-ium 2,2,2-trifluoroacetate The synthesis was carried out as described in Example 20 above.

4.5.24 Example 24

3-(bis(2-methoxyethyl)amino)-1,9-dichloro-7-(pyrrolidin-1-yl)phenothiazin-5-ium 2,2,2-trifluoroacetate The synthesis was carried out as described in Example 20 above.

4.5.25 Example 25

7-(bis(2-methoxyethyl)amino)-3H-phenothiazin-3-one

4.5.25.1 Synthesis of Phenothiazin-5-ium Tetraiodide Hydrate

Phenothiazine (566 mg, 2.84 mmol) was dissolved in $CHCl_3$ (20 mmol) and cooled to 5° C. To this solution was added a solution of 12 (2.16 g, 8.51 mmol) dissolved in $CHCl_3$ (50 mmol) was added over the course of 1 h. The reaction was stirred for 1 h more at 5° C. and a dark solid precipitated. The solid was stirred in ethyl ether for 1 h and filtered. The solid was dried under vacuum to give a quantitative yield of 2.00 g.

4.5.25.2 Synthesis of 3-Aminophenothiazin-5-ium Triiodide

The phenothiazin-5-ium 1.65 g, 2.34 mmol) was dissolved in $CHCl_3$ and pyrrolidine (0.39 mL, 4.67 mmol) was added dropwise. The mixture was stirred at RT for 48 h. The solvent was decanted and the solid was washed three times with ethyl ether. The crude material was used without purification.

4.5.25.3 Synthesis of 7-Amino-3H-phenothiazin-3-one

The crude product isolate from the previous step was dissolved in 1,4-dioxane (10 mmol) and to this solution was added an 8.0 M KOH solution (10 mL). The reaction was warmed to 70° C. with rapid stirring and the color of the solution became dark purple. After 1 h, the reaction was allowed to cool to RT and the layers separated. The aqueous layer was washed with Ethyl Acetate and the combined organic layers were dried over $MgSO_4$, filtered and evaporated to give a residue. The residue was purified to give a dark colored product that was confirmed by LCMS.

4.5.26 Example 26

7-(bis(2-methoxyethyl)amino)-3-oxo-3H-phenothiazine-1-carbonitrile

The synthesis was carried out as described in Example 25 above.

4.5.27 Example 27

7-(bis(2-methoxyethyl)amino)-1,9-dimethyl-3H-phenothiazin-3-one

The synthesis was carried out as described in Example 25 above.

4.6 Biological Activity

4.6.0.1 Respiratory Viruses

The activities of compounds of the invention were determined for the following viruses using the protocol below:
Corona Virus on MRC5 Cells
Influenza Virus A on MDCK Cells
Respiratory Syncytial Virus on HEp2 cells
Adenovirus serotype 5 on A549 cells
Human Rhinovirus on H1Hela Cells
Herpes Simplex Virus 1 on Vero cells Virus was grown in the presence of four dilutions (10 µM, 2 µM, 0.4 µM and 0.08 µM) of the chemical compound tested with two controls using standard methods and materials for the relevant virus. The infected cell extract was collected using known methods, and the infectious virus concentration was determined using standard techniques.

Each well was titrated by $TCID_{50}$. Four serial dilutions in quadruplicate required to determine the titer of each well. To assay 36 replicates as directed, one hundred eight (108) 96-well plates is required. Each drug was tested at four dilutions against one virus will require $TCID_{50}$ titers of 18 sample wells.

4.6.0.2 Monkey Pox Virus

Compounds of the invention were tested for activity against monkey pox virus using the following protocol:
1. Infected cells with target dose of 100 PFU/well MPXV.
2. One hour later, removed the virus solution and wash cells with media and aspirated.
3. Added serial half-log dilutions of compounds in methyl cellulose to triplicate wells; methyl cellulose is semi-solid media which contains virus in one location, so only the adjacent cells are infected. Each plate included a positive control of virus only wells (triplicate), with methyl cellulose overlay.
4. Four days later, removed the media from wells and added crystal violet to stain the cells.
5. After 20 min to 30 min later, washed the cells with $ddH_2O$ and dried.
6. Counted the plaques.
7. Compared plaque numbers of compound wells with the plaque numbers in virus only wells and determined the difference (percentage) of inhibition vs. protection.

4.6.0.3 Marburg Virus

Compounds of the invention were tested against Marburg virus using the following protocol:

Dimethylsulfoxide (DMSO) in 5 mM concentration was used as a solvent for the compounds and as a control. The compounds tested were stored under argon. Each compound was provided in a vial. The experiments were performed on 24-well plate.

Incubation of Compounds With Cells.

Day 0: Plated Vero cells at $1\times10^5$ cells/well in a 1 mL volume of medium (24-well plate), and incubated overnight.

Day 1:
1. Following sterile procedure, diluted each of the four compound stocks in DMSO to concentrations 100-fold greater than will be used in the treatment wells.
2. Further diluted the DMSO stocks 1:100 in EMEM with 10% FBS/Pen/Strep to generate treatments containing 1% DMSO. To generate DMSO control media, diluted DMSO (no compound) to 1% in EMEM with 10% FBS/Pen/Strep.
3. Aspirated the media in cell plates and added 1 mL of compound or control to the appropriate wells.
4. Incubated plate overnight.

Day 2:
1. Dilute virus: Diluted MARV to a concentration of $1\times10^6$ pfu/mL EMEM with 10% FBS/Pen/Strep.
2. Infection: Removed media from wells and applied 100 µL diluted virus to each well, except mock-infected well. Applied 100 µL EMEM with 10% FBS to the mock-infected well. Incubated the plate for 1 h at 37° C., rocking the plate gently every 15 min to prevent the cell monolayer from drying out.
3. Wash cells and add compound: After the one-hour infection period, aspirated the virus from the wells and add 1 mL PBS to each well. Aspirated the PBS and immediately added 1 mL diluted compound to the appropriate wells. The DMSO control and mock-infected wells received 1 mL of the DMSO control media.
4. Critical Treatments:
   (a) Compound Treatment Wells
   (b) DMSO control media+virus
   (c) DMSO control media no virus (Mock)
5. Incubated the plates at 37° C. under 5% $CO_2$ for 72 h.

Day 3: Removed as much media as possible from each well and stored at −80° C.

Determination of Plaques.

Day 0: Seeded 6-well plates with $2.5×10^5$ Vero cells/well in 2 mL volumes of medium. Incubated overnight.

Day 1:
1. In deep-well 96-well plates prepared six 1:10 serial dilutions of supernatants from each well beginning with 1:10 and ending with 1:6 in 500 µL volumes EMEM with 2% FBS:
   (a) Diluted 60 µL undiluted supe into 540 µL EMEM with 2% FBS=1:1.
   (b) Diluted 60 µL of the 1:1 supe into 540 µL EMEM with 2% FBS=1:2.
   (c) Diluted 60 µL of the 1:2 supe into 540 µL EMEM with 2% FBS=1:3.
   (d) Diluted 60 µL of the 1:3 supe into 540 µL EMEM with 2% FBS=1:4
   (e) Diluted 60 µL of the 1:4 supe into 540 µL EMEM with 2% FBS=1:5
   (f) Diluted 60 µL of the 1:5 supe into 540 µL EMEM with 2% FBS=1:6
2. Prepared 2% agarose and place in a 37° C. water bath to prevent the solution from solidifying. Prewarm 2×EMEM in a 37° C. water bath.
   (a) Volume of agarose needed=12 mL per undiluted supe sample+extra.
   (b) Volume of 2×EMEM needed is the same.
3. Removed culture supernatant from plated cells and add 200 µL of diluted culture supernatant in duplicate to appropriate wells, according to plate diagram.
4. Incubated each plate for 1 h at 37° C. under 5% $CO_2$, rocking the plate gently every 15 minute.
5. After plates had incubated for 1 h, combined the 2% agarose with the 2×EMEM and mixed well. Gently applied 2 mL overlay to each well without removing the inoculum and swirled the plate gently to mix the inoculum in with the overlay. Repeated this process to apply overlays to each plate.
6. Allowed the overlays to solidify at room temperature for 1 h.
7. Incubated the plates for 5 d at 37° C. under 5% $CO_2$.
8. Stained the cells using a secondary overlay containing neutral red and incubate for 24 h.
9. Quantified the plaques in each well.

4.6.0.4 Influenza Virus

Compounds of the invention were tested for activity against Influenza virus using the following protocol:
1. MDCK (Madin-Darby canine kidney) cells were plated in three 96-well plates ($6×10^4$ per well) and cultured overnight. The next day the cells were inspected with a microscope to document the confluence. The required amount of wells were infected with the fowl plaque virus (Influenza A/H7N7/Bratislava/1979) with an MOI of 1 (assuming duplication of cells over night to generate $1.2×10^5$ PFU/well). Infection was performed with 200 µL of virus suspension. All three plates were treated identically and served as triplicates. On each plate was one well with one concentration of substance, three wells with the highest concentration of DMSO that is used on the plate, and three wells with the lowest concentration of DMSO that is on the plate. In addition there were three infected wells that were cultured with cell culture medium without additional substance. There also were 12 wells on every plate that were not infected and served as controls for the cpe determination and for the neutral red staining.
2. Substances were diluted before cells were infected and plates in 96-well plates so that they could easily be plated on the infected cells.
3. Infection was performed for 30 min at 37° C. in a cell culture incubator.
4. After infection the cells were washed once with infection-PBS. During washing the cell monolayer was inspected with a microscope, and damaged monolayers were excluded from testing. Uninfected wells were mock infected with infection-PBS and also inspected visually.
5. The pattern of substances on every individual plate was marked on the top of the plate and on a scheme.
6. An aliquote of 250 µL of diluted substance was used and cells were incubated for 16 h. After incubation time the cell monolayer was again inspected and cpe was monitored and recorded.
7. Supernatants of the first plate were transferred to a 96-well ELISA-plate and kept cool for titration, which was performed later the same day.
8. Cells of this plate were washed carefully with PBS again inspected at the microscope and then stained with neutral red (which is staining the living cells) for 3 hours at 37° C. (neutral red is used at the concentration 1 mg/20 mL MEM; 200 µL/well.
9. In the meantime the dilutions for the titration were generated in a 96-well plate by diluting the supernatants 1:10. A 100 µL aliquot of undiluted supernatant and five dilutions (from $10^{-1}$ to $10^{-5}$ were used to infect 24-wells of MDCK monolayers of cells. This means that at this time point we only titrate one unique copy of every tested substance. The other three plates were immediately frozen at −70° C. and stored until titration.
10. The neutral red staining was stopped by washing the monolayer three times very carefully with PBS and the plate was dried on cellulose to eliminate residual PBS.
11. The neutral red was dissolved from the cells by using Ethanol/acidic acid for min on a plate rocking platform.
12. The Ethanol/acidic acid was transferred to an Elisa-plate and measured at 570 nm in an Elisa-reader.
13. The percentage of live cells was calculated setting the non-infected cells to 100%.

4.6.0.5 Ebola Virus

Compounds of the invention were tested for activity against Ebola virus using the following protocol:

Concentration of Compound: 10 mM DMSO stock. Day 0: Vero cells were plated at $1×10^5$ cells/well in a 1 mL volume of medium (24-well plate), and incubate overnight.

Day 1: Compound Dilutions
1. Following sterile procedure, diluted each of the four compound stocks in DMSO to concentrations 100-fold greater than will be used in the treatment wells.
2. Further diluted the DMSO stocks 1:100 in EMEM with 10% FBS/Pen/Strep to generate treatments containing 1% DMSO. To generate DMSO control media, diluted DMSO (no compound) to 1% in EMEM with 10% FBS/Pen/Strep.
3. Aspirated the media in cell plates and add 1 mL of compound or control to the appropriate wells
4. Incubated plate overnight. .

Day 2:
1. Diluted virus: Diluted EBOV to a concentration of 1×10$^6$ PFU/mL Eagle's Minimum Essential Medium (EMEM) with 10% FBS/Pen/Strep.
2. Infection: Removed media from wells and applied 100 μL diluted virus to each well, except mock-infected well. Applied 100 μL) EMEM with 10% FBS to the mock-infected well. Incubated the plate 1 h at 37° C., rocking the plate gently every 15 min to prevent the cell monolayer from drying out.
3. Washed cells and added compound. After the 1 h infection period, aspirated the virus from the wells and added 1 mL PBS to each well. Aspirated the PBS and immediately added 1 mL diluted compound to the appropriate wells. The DMSO control and mock-infected wells received 1 mL of the DMSO control media.
4. Critical Treatments:
   (a) Compound Treatment Wells
   (b) DMSO control media+virus
   (c) DMSO control media no virus (Mock)
   5. Incubated the plates: Incubated the plates at 37° C. under 5% $CO_2$ for 72 h.

Day 3:

Removed the supernatant from infected plates: Removed as much media as possible from each well and stored at −80° C.

Plaque Assay:

Day 0:

1. Seeded 6-well plates with $2.5\times10^5$ Vero cells/well in 2 mL volumes of medium. Incubated overnight.

Day 1:

1. In deep-well 96-well plates prepared six 1:10 serial dilutions of supernatants from each well beginning with 1:10 and ending with $1{:}10^6$ in 500 μL volumes of EMEM with 2% FBS:
   (a) Diluted 60 μL undiluted supe into 540 μL EMEM with 2% FBS=1:101.
   (b) Diluted 60 μL of the $1{:}10^1$ supe into 540 μL EMEM with 2% FBS=$1{:}10^2$.
   (c) Diluted 60 μL of the $1{:}10^2$ supe into 540 μL EMEM with 2% FBS=$1{:}10^3$.
   (d) Diluted 60 μL of the $1{:}10^3$ supe into 540 μL EMEM with 2% FBS=$1{:}10^4$
   (e) Diluted 60 μL of the $1{:}10^4$ supe into 540 μL EMEM with 2% FBS=$1{:}10^5$
   (f) Diluted 60 μL of the $1{:}10^5$ supe into 540 μL EMEM with 2% FBS=$1{:}10^6$
2. Prepared 2% agarose and placed in a 37° C. water bath to prevent the solution from solidifying. Prewarmed 2×EMEM in a 37° C. water bath.
   (a) Volume of agarose needed=12 mL per undiluted supe sample+extra.
   (b) Volume of 2×EMEM needed is the same.
3. Removed culture supernatant from plated cells and added 200 μL of diluted culture supernatant in duplicate to appropriate wells, according to plate diagram.
4. Incubated each plate for 1 h at 37° C. under 5% $CO_2$, rocking the plate gently every 15 min.
5. After plates had incubated for 1 h, combined the 2% agarose with the 2×EMEM and mixed well. Gently applied 2 mL overlay to each well without removing the inoculum and swirled the plate gently to mix the inoculum in with the overlay. Repeated this process to apply overlays to each plate.
6. Allowed the overlays to solidify at room temperature for 1 h.

7. Incubated the plates for 5 d at 37° C. under 5% $CO_2$.
8. Stained the cells using a secondary overlay containing neutral red and incubated for 24 h.
9. Quantified the plaques in each well.

4.6.0.6 Dengue, Easter Equine Encephalitis, Venezuelan Equine Encephalitis, Western Equine Encephalitis, West Nile, and Chikungunya Viruses Compounds of the invention were tested for activity against Dengue, Easter Equine Encephalitis, Venezuelan Equine Encephalitis, Western Equine Encephalitis, West Nile, and Chikungunya Viruses using the following protocol:

1. The Set test sample was set up in ten-fold dilutions across a 96-well plate. A mixture of 270 μL HBSS with HEPES and 2% FBS with Pen/Strep or complete media 2% FBS was added to each well. To the first well in each row 30 μL of test sample was introduced (i.e, a 1:10 dilution) and mixed. A 30 μL aliquot was transferred from the first well to next well, and so on. Dilutions out to well #9 were made to provide a range of dilutions from $10^{-1}$ to $10^{-9}$. Be sure to discard tips between transfers.
2. Once dilutions were ready the plates were labeled with sample number and dilutions (plates can be labeled at any time prior to infection). Each dilution was plated on two wells. If plating dilutions $10^{-1}$ to $10^{-9}$, requires three plates per sample.
3. The media was removed from six-well plates by inverting over a dispo pan containing microchem disinfectant. Then 100 μL was added to each well of virus dilution. A duplicate was done to obtain an average. The plates were incubated at 37° C., 5% $CO_2$ for 1 h with occasional rocking (approximately every 15 min).
4. Preparation of media and agarose for overlay. Final concentration 1×EMEM, 10% FBS, 1% Pen/Strep, 0.1% gentamycin, in a 0.6% agarose solution (see cell culture overlay without neutral red chart). Added about 2 mL of overlay to each well and returned to the incubator. (It is not necessary to allow to solidify prior to placing in the incubator.) Incubated overnight at 37° C., 5% $CO_2$.
5. Next day: The resulting plaques were visualized with Neutral Red. A media/agarose overlay was prepared as above with 4% neutral red solution added to the media/agarose overlay as prepared in Step 4 (see cell culture overlay with neutral red overlay chart). Added about 2 mL ml per well.
6. Incubated the plates overnight at 37° C., 5% $CO_2$.
7. Counted plaques.

4.6.0.7 HIV Virus

H9 cells were obtained from the AIDS Research and Reference Reagent Program. A chronically infected cell population was generated by infection with HIV-1 SK-1 (references 1 & 2 below) and long term culture. Cells were maintained under standard culture conditions in RPMI 1640 supplemented with 15% fetal bovine serum (heat inactivated), 2 mM L-glutamate, 100 U $mL^{-1}$ penicillin and 100 μg $mL^{-1}$ streptomycin. Cultures are maintained in such a way as to ensure exponential growth of the populations. At the time of the assay cells are collected by centrifugation and counted by hemacytometer. If cell viability by Trypan Blue dye exclusion is less than 90% the assay is terminated. The cells are adjusted to $3\times10^5$ cells $mL^{-1}$ and 100 μL placed in 96-well plates with 100 μL media containing the test compound. Cultures are incubated for 3 d and supernatants harvested. Compound toxicity is determined by MTS dye reduction. Virus expression is measured by supernatant reverse transcriptase activity and subsequent determination of supernatant virus infectivity by MAGI assay.

Reverse Transcriptase Activity Assay

A microtiter plate-based reverse transcriptase (RT) reaction was utilized (Buckheit et al., *AIDS Research and Human Retroviruses* 7:295-302, 1991). Tritiated thymidine triphosphate ($^3$H-TTP, 80 Ci mmol$^{-1}$, NEN) was received in 1:1 dH$_2$O:Ethanol at 1 mCimL$^{-1}$. Poly rA:oligo dT template: primer (Pharmacia) was prepared as a stock solution by combining 150 μL poly rA (20 mg mL$^{-1}$ with 0.5 mL oligo dT (20 U mL$^{-1}$) and 5.35 mL sterile dH$_2$O followed by aliquoting (1.0 mL) and storage at −20° C. The RT reaction buffer was prepared fresh on a daily basis and consists of 125 μL 1.0 M EGTA, 125 μL dH$_2$O, 125 μL 20% Triton X100, 50 μL 1.0 M Tris (pH 7.4), 50 μL 1.0 M DTT, and 40 μL 1.0 M MgCl$_2$. The final reaction mixture was prepared by combining 1 part $^3$H-TTP, 4 parts dH$_2$O, 2.5 parts poly rA:oligo dT stock and 2.5 parts reaction buffer. Ten microliters of this reaction mixture was placed in a round bottom microtiter plate and 15 μL of virus containing supernatant was added and mixed. The plate was incubated at 37° C. for 60 min. Following incubation, the reaction volume was spotted onto DE81 filter-mats (Wallac), washed 5 times for 5 min each in a 5% sodium phosphate buffer or 2×SSC (Life Technologies). Next they were washed 2 times for 1 min each in distilled water, 2 times for 1 min each in 70% ethanol, and then dried. Incorporated radioactivity (counts per minute, CPM) was quantified using standard liquid scintillation techniques.

MTS Staining for Cell Viability

At assay termination, assay plates were stained with the soluble tetrazolium-based dye MTS (3-(4,5-dimethylthiazol-2-yl)-5-(3-carboxymethoxyphenyl)-2-(4-sulfophenyl)-2H-tetrazolium; CellTiter 96 Reagent, Promega) to determine cell viability and quantify compound toxicity. The mitochondrial enzymes of metabolically active cells metabolize MTS to yield a soluble formazan product. This allows the rapid quantitative analysis of cell viability and compound cytotoxicity. The MTS is a stable solution that does not require preparation before use. At termination of the assay, 20 μL of MTS reagent was added per well. The microtiter plates were then incubated 4 h to 6 h at 37° C. The incubation intervals were chosen based on empirically determined times for optimal dye reduction. Adhesive plate sealers were used in place of the lids, the sealed plate was inverted several times to mix the soluble formazan product and the plate was read spectrophotometrically at 490/650 nm with a Molecular Devices SPECTRAMAXPLUS plate reader.

Determination of Virus Infectivity Using MAGI Cells

This assay uses MAGI cells (HeLa-CD4-LTR-β-gal cells; AIDS Research and Reference Reagent Repository, Bethesda, Md.), that contain one copy of the HIV-1 LTR promoter that drives expression of the β-galactosidase gene upon HIV-1 Tat transactivation. Thus, the expression of β-galactosidase was measured as a function of virus infection of the cells. Twenty-four hours prior to initiation of the assay, MAGI cells were plated in 96 flatwell plates. On the day of the assay, media was removed from the wells and 50 μL of supernatant was transferred from the ACH-2 or H9/SK-1 cultures onto the MAGI cells. The plates were incubated for 1 h at 37° C. Fresh media (150 μL was then added to the wells for a final volume of 200 μL. Plates were incubated for 7 d. A chemiluminescent endpoint was used to determine the extent of β-galactosidase expression as a measure of HIV-1 infection of the cells. At 7 d post infection, plates were aspirated and PBS was added to each well. Subsequently, detection of β-galactosidase activity was determined by measurement of relative chemiluminescence per manufacturer's instructions (TROPIX GAL-screen, Applied Biosystems, Bedford, Mass.).

Data Analysis

The IC$_{50}$ (50%, inhibition of virus replication) was calculated, TC$_{50}$ (50% reduction in cell viability), and a therapeutic index (TI=TC$_{50}$/IC$_{50}$) were determined.

References

The following references are incorporated in there entireties and for all purposes.
1. Cloyd, M. W., and B. E. Moore. 1990. Spectrum of biological properties of human immunodeficiency virus (HIV-1) isolates. *Virology* 174:103-116.
2. C. Lackman-Smith, et al. 2008. Development of a Comprehensive Human Immunodeficiency Virus Type 1 Screening Algorithm for Discovery and Preclinical Testing of Topical Microbicides. *Antimicrobial Agents & Chemotherapy* 52(5):1768-1781.

HCV Live Virus Assay

HCV infection in cell culture was performed using Huh7 hepatoma cells transduced with a lentiviral vector containing a Gaussia luciferase reporter (G-Luc) gene as reported previously (see below); the luciferase reporter is secreted into the media and provides a convenient measure of cell number and viability. Measurement of virus replication (RNA replication, assembly, release, and infection) was enhanced by including a firefly luciferase reporter gene into the context of the Jc1 chimera. Since the firefly luciferase and the gaussia-luciferase utilize different substrates (luciferin, and coelenteracine, respectively) and were cell associated or secreted, respectively, both HCV replication and cell viability could be determined in parallel.

Jc1-F-Luc was transfected into Huh7-G-Luc cells and the test compound was added after four hours. Forty-eight hours post transfection (44 hours after compound addition), the media was removed and added to nave cells. Another 48 h later the inoculated cells were harvested and both firefly and gaussia luciferase activity was determined. In this assay format, the firefly luciferase activity was proportional to the efficiency of HCV replication in transfected cells, assembly of progeny particles in the transfected cells, the infectivity of the released particles and replication in the infected cells. Therefore, this type of assay interrogates the complete viral life cycle, in principle allowing detection of interference with any phase of the viral replication process. Using cells transfected with subgenomic HCV replicons (lacking the structural proteins) we will specifically assess possible effects of selected compounds on HCV RNA replication and translation. Finally we will employ HCV pseudoparticles (HCVpp); i.e. retroviral or lentiviral cores surrounded by an envelope containing HCV glycoproteins to selectively analyze interference of any of the compounds with HCV entry. In addition to the HCV specific firefly luciferase signals we will assess gaussia luciferase activity to monitor cell number and viability. During the initial screening each individual compound will be analyzed in three different doses. Based on the HCV-specific dose response, compounds will be prioritized for more detailed characterization.

The following references are incorporated in there entireties and for all purposes.
1. Wakita, T. et al. "Production of infectious hepatitis C virus in tissue culture from a cloned viral genome." *Nat Med* 11, 791-6 (2005).
2. Zhong, J. et al. "Robust hepatitis C virus infection in vitro." *Proc Natl Acad Sci USA* 102, 9294-9 (2005).

3. Koutsoudakis, G. et al. "Characterization of the early steps of hepatitis C virus infection by using luciferase reporter viruses." *J Virol* 80, 5308-20 (2006).
4. Pietschmann, T. et al. "Construction and characterization of infectious intragenotypic and intergenotypic hepatitis C virus chimeras." *Proc Natl Acad Sci USA* 103, 7408-13 (2006).
5. de Chassey, B. et al. "Hepatitis C virus infection protein network." *Mol Syst Biol* 4, 230 (2008).
6. Bartosch, B., Dubuisson, J. & Cosset, F. "Infectious hepatitis C virus pseudoparticles containing functional E1-E2 envelope protein complexes." *J Exp Med* 197, 633-42 (2003).
7. Hsu, M. et al. "Hepatitis C virus glycoproteins mediate pH-dependent cell entry of pseudotyped retroviral particles." *Proc Natl Acad Sci USA* 100, 7271-6 (2003)

Certain compounds of the invention were tested for their activity against several different viruses using standard live virus assays known to those having ordinary skill in the art. The viruses stuided were Human Immunodficiency Virus (HIV), Hepatitis C Virus (HCV), Influenza (FLUV), Venezuelean Equinne Encephalitis Virus (VEEV), Rift Valley Fever Virus (RVFV), and Lhassa Virus (LASV). The results of the tests are provided below.

Results for 3,7-bis(bis(2-methoxyethyl)amino)-1,9-dimethylphenothiazin-5-ium bromide

| Virus | HIV | HCV | FLUV | VEEV | RVFV | LASV |
|---|---|---|---|---|---|---|
| $EC_{50}$ (µM) | 0.1-0.5 | 1 | 0.25-1 | 1 | 1-10 | >1 |
| $EC_{99}$ (µM) | 0.1-0.5 | 7.5-10 | 1-4 | 1-7.5 | 1-10 | >1 |

Results for 3-(Bis(2-methoxyethyl)amino)-7-(pyrrolidin-1-yl)phenothiazin-5-ium iodide

| Virus | HIV | HCV | FLUV | VEEV | RVFV | LASV |
|---|---|---|---|---|---|---|
| $EC_{50}$ (µM) | >1 | NA | 2 | >20 | NA | NA |
| $EC_{50}$ (µM) | >1 | NA | 2-8 | >20 | NA | NA |

Results for 3,7-bis(bis(2-methoxyethyl)amino)-1,9-dichlorophenothiazin-5-ium 2,2,2-trifluoroacetate

| Virus | HIV | HCV | FLUV | VEEV | RVFV | LASV |
|---|---|---|---|---|---|---|
| $EC_{50}$ (µM) | NA | 2.5 | >10 | 5 | 0.1 | 5 |
| $EC_{99}$ (µM) | NA | 10 | >10 | >5 | >5 | >5 |

Results for 3,7-bis(bis(2-methoxyethyl)amino)-1-chlorophenothiazin-5-ium 2,2,2-trifluoroacetate

| Virus | HIV | HCV | FLUV | VEEV | RVFV | LASV |
|---|---|---|---|---|---|---|
| $EC_{50}$ (µM) | NA | NA | NA | 0.4 | 0.4 | >1 |
| $EC_{99}$ (µM) | NA | NA | NA | >1 | >1 | >1 |

Results for 9-ethyl-N,N-bis(2-methoxyethyl)-1-methyl-3-(pyrrolidin-1-yl)-3H-phenothiazin-7-amine

| Virus | HIV | HCV | FLUV | VEEV | RVFV | LASV |
|---|---|---|---|---|---|---|
| $EC_{50}$ (µM) | NA | 0.25 | NA | NA | NA | NA |
| $EC_{99}$ (µM) | NA | NA | NA | NA | NA | NA |

5 CONCLUSION

The above description of the embodiments, alternative embodiments, and specific examples, are given by way of illustration and should not be viewed as limiting. Further, many changes and modifications within the scope of the present embodiments may be made without departing from the spirit thereof, and the present invention includes such changes and modifications.

What is claimed:
1. A compound having the structure:

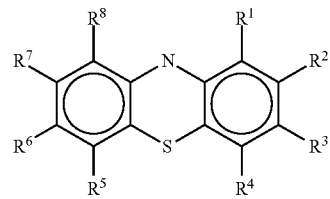

and its pharmaceutically acceptable salts and hydrates, wherein:

$R^1$, $R^2$, $R^4$, $R^5$, $R^7$, and $R^8$ are selected independently from the group consisting of: hydrogen, halo, cyano, nitro, amino, carboxyl, formyl, and optionally substituted alkyl, alkylcarbonyloxy, arylcarbonyloxy, heteroarylcarbonyloxy, cycloalkylcarbonyloxy, cycloheteroalkylcarbonyloxy, aralkycarbonyloxy, heteroaralkylcarbonyloxy, (cycloalkyl)alkylcarbonyloxy, (cyclohetroalky)alkylcarbonyloxy, alkylcarbonyl, arylcarbonyl, heteroarylcarbonyl, cycloalkycarbonyl, cyclohetroalkycarbonyl, aralkycarbonyl, heteroaralkylcarbonyl, (cycloalkyl)alkylcarbonyl, (cycloheteroalkyl)alkylcarbonyl, alkylaminocarbonyl, arylaminocarbonyl, aralkylaminocarbonyl, heteroarylaminocarbonyl, heteroaralkylaminocarbonyl, alkylcarbonylamino, arylcarbonylamino, heteroarylcarbonylamino, cycloalkylcarbonylamino, cycloheteroalkylcarbonylamino, aralkylcarbonylamino, heteroaralkylcarbonylamino, (cycloalkyl)alkylcarbonylamino, (cyclohetroalky)alkylcarbonylamino, dialkylamino, arylarmino, diarylamino, aralkylamino, diaralkylamino, heteroarylamino, diheteroarylamino, heteroaralkylamino, diheteroaralkylamino, alkylsulfonyl, arylsulonyl, heteroarylsuonyl, cycloalkylsulfonyl, alkyloxycarbonyl, aryloxycarbonyl, heteroaryloxycarbonyl, cycloalkyloxycarbonyl, cycloheteroalkyloxycarbonyl, aralyoxycabhonyloxloxycarbonyl, heteroaralkyloxycarbony, (cycloalkyl)alkyloxycarbonyl, (cyclohetroalky)alkyloxycarbony, iminoalkyl, iminocycloalky, iminocycloheteroalkyl, iminoaralkyl, iminohetroaralkyl, (cycloalkyl)iminoalkyl, and (cycloheteroalkyl)iminoalkyl;

at least one of $R^1$ and $R^8$ is selected from the group consisting of: halo, nitro, cyano, carboxyl, formyl, and optionally substituted alkyl $R^3$ and $R^6$ are selected independently from the group consisting of: imino, and optionally substituted dialkylimino, diarylimino, di-heteroarylimino, alkylarylimino, alkylheteroarylimino, arylheteroarylimino, alkyloxyalkylamino, di-(alkyloxyalkyl)amino, aryloxyalkylamino, di-(aryloxyalkyl)amino, arylaminoalkylamino, di-(arylaminoalky)amino, heteroaryloxyalkylamino, di-(heteroaryloxyalkyl)amino, heteroarylaminoalkylamino, di-(heteroarylaminoalky) amino, and cycloalkylamino; and at least one of $R^3$ and $R^6$ is selected from the group consisting of: alkyloxyalkylamino, di-(alkyloxyalkyl)amino, aryloxyalkylamino, di-(aryloxyalkyl)amino, arylaminoalkylamino, di-(arylaminoalkyl)amino, heteroaryloxyalkylamino, di-(heteroaryloxyalky)amino, heteroarylaminoalkylamino, and di(heteroarylaminoalkylene)amino;

wherein said optionally substituted is with a group which is hydrooxyl, nitro, amino, imino, cyano, halo, amidino, oxo, α-amidino, methoxamidino, imidino, guanidino, sulfonamido, carboxyl, formyl, lower alkyl, haloloweralkyl, loweralkoxy, haloloweralkoxy, lower alkoxyalkyl, alkylcarbonyl, arylcarbonyl, aralkylcarbonyl, heteroarylcarbonyl, heteroaralkylcarbonyl, aminoalkyl, or cyanoalkyl.

2. A compound of claim 1, wherein $R^3$ is selected from the group consisting of: alkyloxyalkylamino, di-(alkyloxyalkyl)amino, alkylaminoalkylamino, di-(alkylaminoalkyl)amino, aryloxyalkylamino, di-(aryloxyalkyl)amino, arylaminoalkylamino, di(arylaminoalkylene)amino, heteroaryloxyalkylamino, di(heteroaryloxyalkylene)amino, heteroarylaminoalkylamino, and di-(heteroarylaminoalkyl)amino.

3. A compound of claim 1, wherein at least one of $R^1$ and $R^8$ selected from the group consisting of: halo, carboxyl, and optionally substituted alkyl.

4. A compound of claim 3, wherein at least one of $R^1$ and $R^8$ is selected from the group consisting of: halo, carboxyl, and optionally substituted alkyl.

5. A compound of claim 4, wherein at least one of $R^1$ and $R^8$ is halo.

6. A compound of claim 5, wherein least one of $R^1$ and $R^8$ is fluoro.

7. A compound of claim 5, wherein least one of $R^1$ and $R^8$ is chloro.

8. A compound of claim 5, wherein $R^1$ and $R^8$ are both halo.

9. A compound of claim 8, wherein $R^1$ and $R^8$ are both fluoro.

10. A compound of claim 8, wherein $R^1$ and $R^8$ are both chloro.

11. A compound of claim 1, wherein at least one of $R^1$ and $R^8$ is selected from the group consisting of: halo, carboxyl, and optionally substituted alkyl.

12. A compound of claim 11, wherein at least one of $R^1$ and $R^8$ is halo.

13. A compound of claim 12, wherein at least one of $R^1$ and $R^8$ is fluoro.

14. A compound of claim 12, wherein at least one of $R^1$ and $R^8$ is chloro.

15. A compound of claim 12, wherein $R^1$ and $R^8$ are both halo.

16. A compound of claim 15, wherein $R^1$ and $R^5$ are both fluoro.

17. A compound of claim 15, wherein $R^1$ and $R^8$ are both chloro.

18. A method for treating a viral disease in a mammal afflicted with such disease, comprising administering to such mammal a therapeutically effective amount of the compound of claim 1.

19. A compound of claim 1, which is 3,7-bis(bis(2-methoxyethyl)amino)-1,9-dimethylphenothiazin-5-ium.

20. A compound of claim 11, which is 3,7-bis(bis(2-metboxyethyl)amino)-1,9-dimethylphenothiazin-5-ium, 3,7-bis(bis(2-ethoxyethyl)amino)-1,9-diisopropylphenothiazin-5-ium, 3,7-bis(bis(2-methoxyethyl)amino)-1-methylphenothiazin-5-ium,3,7-bis(bis(2-methoxyethyl)amino)-1-isopropylphenothiazin-5-ium,3,7-bis(bis(2-methoxyethyl)amino)-1-(tert-butyl)phenothiazin-5-ium, 3,7-bis(bis(2-methoxyethy)amino)-1-butylphenothiazin-5-ium, 3,7-bis(bis(2-methoxyethyl)amino)-1-(trifluoromethyl)phenothiazin-5-ium, 3,7-bis(bis(2-methoxyethyl)amino)-1,9-diethylphenothiazin-5-ium, 7-(bis(2-methoxyethyl)amino)-3-(4-(tert-butoxycarbonyl)piperazin-1yl)-1-ethylphenothiazin-5-ium, 3-(bis(2-methoxyethyl)amino)-7-(4-(tert-butoxycarbonyl)piperazin-1-yl)-1-ethylphenothiazin-5-ium, 3-(bis(2-methoxyethyl)amino)-7-(dimethylamino)-1-(trifluoromethyl)phenothiazin -5-ium, or 3,7-bis(bis(2-methoxyethyl)amino)-1-chlorophenothiazin-5-ium.

21. A compound of claim 17, which is 3,7-bis(bis(2-methoxyethyl)amino)-1,9-dichlorophenothiazin-5-ium, 3-(bis(2-methoxyethyl)amino)-1,9-dichloro-7-(pyrrolidin-1-yl)phenothiazin-5-ium, or 3-(bis(2-methoxyethyl)amino)-1,9-dichloro-7-(piperazin-1yl)phenothiazin-5-ium.

22. A method of claim 18, wherein said viral disease is selected from the group consisting of HCV, HIV, influenza, Ebola virus, Marburg virus, Dengue virus, Venezuelean equine encephalitis, Easter Equine Encephalitis, Western Equine Encephalitis, Chikungunya virus, Monkey Pox, Corona Virus, Respiratory Syncytial Virus, Adenovirus, Human Rhinovirus, Herpes Simplex Virus, and West Nile virus.

23. A compound of claim 1, which is 7-(bis(2-methoxyethyl)amino)-1-ethyl-3-(piperazin-1-yl)phenothiazin-5-ium or 3-(bis(2-methoxyethyl)amino)-1-ethyl-7-(piperazin-1-yl)phenothiazin-5-ium.

24. A compound of claim 1, which is 7-(bis(2-methoxyethyl)amino)-3-(piperazin-1-yl)-1-(trifluoromethyl)phenothiazin-5-ium or 7-(bis(2-methoxyethyl)-amino)-3-(4-(tert-butoxycarbonyl)piperazin-1-yl)-1-ethylphenothiazin-5-ium.

* * * * *